(12) United States Patent
McLaughlin et al.

(10) Patent No.: US 11,931,464 B2
(45) Date of Patent: *Mar. 19, 2024

(54) MINIMIZING AGGLOMERATION, AERATION, AND PRESERVING THE COATING OF PHARMACEUTICAL COMPOSITIONS COMPRISING IBUPROFEN

(71) Applicant: Catalent U.K. Swindon Zydis Limited, Glasgow (GB)

(72) Inventors: Rosaleen McLaughlin, Swindon (GB); Simon Andrew Martyn Howes, Swindon (GB); Craig Wheadon, Swindon (GB); Jonathon Whitehouse, Herne Bay (GB); Adam Parker, Swindon (GB)

(73) Assignee: Catalent U.K. Swindon Zydis Limited, Swindon (GB)

( * ) Notice: Subject to any disclaimer, the term of this patent is extended or adjusted under 35 U.S.C. 154(b) by 122 days.

This patent is subject to a terminal disclaimer.

(21) Appl. No.: 17/387,803

(22) Filed: Jul. 28, 2021

(65) Prior Publication Data

US 2021/0353551 A1 Nov. 18, 2021

Related U.S. Application Data

(63) Continuation of application No. 17/008,108, filed on Aug. 31, 2020, now Pat. No. 11,077,067, which is a
(Continued)

(51) Int. Cl.
*A61K 9/50* (2006.01)
*A61K 31/192* (2006.01)
(Continued)

(52) U.S. Cl.
CPC ............ *A61K 9/5073* (2013.01); *A61K 9/501* (2013.01); *A61K 9/5015* (2013.01);
(Continued)

(58) Field of Classification Search
None
See application file for complete search history.

(56) References Cited

U.S. PATENT DOCUMENTS

| 4,305,502 A | 12/1981 | Gregory et al. |
| 4,371,516 A | 2/1983 | Gregory et al. |

(Continued)

FOREIGN PATENT DOCUMENTS

| CA | 2512988 A1 | 8/2004 |
| CN | 102300558 A | 12/2011 |

(Continued)

OTHER PUBLICATIONS

First Office Action dated Nov. 3, 2022, directed to CN Application No. 202080015446.5; 22 pages.
(Continued)

*Primary Examiner* — Ernst V Arnold
(74) *Attorney, Agent, or Firm* — Morrison & Foerster LLP

(57) ABSTRACT

Provided are pharmaceutical compositions and methods for preparing pharmaceutical compositions comprising Ibuprofen using solventless mixing methods. Excess coating material that is not bound to coated Ibuprofen may be removed by a sieving process. Coating and dosing ratios can also be optimized to minimize the amount of excess unbound coating material. Additionally, the compositions can be formulated to preserve the functional coating of coated Ibuprofen and to minimize aeration of Ibuprofen when mixed into suspension.

5 Claims, 15 Drawing Sheets

Related U.S. Application Data continuation of application No. 16/798,130, filed on Feb. 21, 2020, now Pat. No. 11,166,919.

(60) Provisional application No. 62/809,293, filed on Feb. 22, 2019, provisional application No. 62/809,287, filed on Feb. 22, 2019, provisional application No. 62/809,307, filed on Feb. 22, 2019.

(51) Int. Cl.
*A61K 47/00* (2006.01)
*A61K 47/26* (2006.01)
*A61K 47/36* (2006.01)
*A61K 47/42* (2017.01)

(52) U.S. Cl.
CPC .......... *A61K 9/5089* (2013.01); *A61K 31/192* (2013.01); *A61K 47/26* (2013.01); *A61K 47/36* (2013.01); *A61K 47/42* (2013.01)

(56) References Cited

U.S. PATENT DOCUMENTS

| | | | |
|---|---|---|---|
| 4,758,598 | A | 7/1988 | Gregory |
| 5,008,117 | A | 4/1991 | Calanchi et al. |
| 5,320,848 | A | 6/1994 | Geyer |
| 5,558,880 | A | 9/1996 | Gole et al. |
| 5,976,577 | A | 11/1999 | Green et al. |
| 6,214,386 | B1 | 4/2001 | Santus |
| 6,413,549 | B2 | 7/2002 | Green et al. |
| 6,709,669 | B1 | 3/2004 | Murray et al. |
| 6,951,657 | B1 | 10/2005 | Zuccarelli |
| 9,107,851 | B2 | 8/2015 | Dave et al. |
| 11,026,892 | B2 * | 6/2021 | McLaughlin ........ A61K 9/0056 |
| 11,077,067 | B2 * | 8/2021 | McLaughlin .......... A61K 47/26 |
| 11,141,380 | B2 * | 10/2021 | McLaughlin ........ A61K 9/1658 |
| 11,166,919 | B2 * | 11/2021 | McLaughlin .......... A61K 47/26 |
| 11,185,508 | B2 * | 11/2021 | McLaughlin .......... A61K 47/02 |
| 2003/0185096 | A1 | 10/2003 | Hollstein et al. |
| 2003/0195179 | A1 | 10/2003 | Sawa |
| 2004/0137061 | A1 | 7/2004 | Ishibashi et al. |
| 2004/0170686 | A1 | 9/2004 | Fredrickson et al. |
| 2004/0265373 | A1 | 12/2004 | Wynn et al. |
| 2007/0148099 | A1 | 6/2007 | Burke et al. |
| 2007/0292508 | A1 | 12/2007 | Szamosi et al. |
| 2008/0075825 | A1 | 3/2008 | Fuisz et al. |
| 2008/0096979 | A1 | 4/2008 | Pilgaonkar |
| 2008/0113021 | A1 | 5/2008 | Shen |
| 2008/0311201 | A1 | 12/2008 | Der-Yang et al. |
| 2008/0317853 | A1 | 12/2008 | Kashid et al. |
| 2009/0062241 | A1 | 3/2009 | Bauer |
| 2009/0148524 | A1 | 6/2009 | Higuchi et al. |
| 2011/0229573 | A1 | 9/2011 | Tian |
| 2014/0105936 | A1 | 4/2014 | Limonov et al. |
| 2014/0106059 | A1 | 4/2014 | Dave et al. |
| 2016/0361335 | A1 | 12/2016 | Jacon et al. |
| 2020/0268667 | A1 | 8/2020 | Mclaughlin |
| 2020/0268668 | A1 | 8/2020 | Mclaughlin |
| 2020/0268676 | A1 | 8/2020 | Mclaughlin |
| 2020/0268677 | A1 | 8/2020 | Mclaughlin |
| 2020/0390704 | A1 | 12/2020 | Mclaughlin |
| 2020/0390716 | A1 | 12/2020 | Mclaughlin |
| 2023/0390205 | A1 | 12/2023 | McLaughlin et al. |

FOREIGN PATENT DOCUMENTS

| | | |
|---|---|---|
| CN | 102579390 A | 7/2012 |
| CN | 103169655 A | 6/2013 |
| EP | 0636365 A1 | 2/1995 |
| EP | 1405635 A1 | 4/2004 |
| EP | 1621186 A1 | 2/2006 |
| GB | 211423 A | 2/1924 |
| GB | 1548022 A | 7/1979 |
| JP | H9-511256 A | 11/1997 |
| JP | 2002-012557 A | 1/2002 |
| JP | 2003-055197 A | 2/2003 |
| JP | 2008-517979 A | 5/2008 |
| TW | 512167 B | 12/2002 |
| WO | 92/22369 A1 | 12/1992 |
| WO | 02/47607 A2 | 6/2002 |
| WO | 2004/066925 A2 | 8/2004 |
| WO | 2006/045830 A1 | 5/2006 |
| WO | 2008/036299 A2 | 3/2008 |
| WO | 2009/108775 A2 | 9/2009 |
| WO | 2011/063531 A1 | 6/2011 |
| WO | 2013/024373 A1 | 2/2013 |
| WO | 2013/183062 A2 | 12/2013 |
| WO | 2014/062444 A1 | 4/2014 |
| WO | 2017/080566 A1 | 5/2017 |
| WO | 2020/169989 A1 | 8/2020 |

OTHER PUBLICATIONS

Written Opinion dated Nov. 2, 2022, directed to SG Application No. 11202108659X; 8 pages.
Written Opinion dated Nov. 2, 2022, directed to SG Application No. 11202109104X; 7 pages.
McLaughlin et al., U.S. Office Action dated Aug. 23, 2022, directed to U.S. Appl. No. 16/798,067; 15 pages.
McLaughlin et al., U.S. Office Action dated Dec. 22, 2022, directed to U.S. Appl. No. 16/798,067; 14 pages.
Written Opinion dated Nov. 2, 2022, directed to SG Application No. 11202109022U; 8 pages.
Written Opinion dated Nov. 3, 2022, directed to SG Application No. 11202108690Y; 11 pages.
Anonymous. (2014). "Safety Data Sheet Orange Tincture," located at <https://jmloveridge.com/wp-content/uploads/2018/06/Orange-Tincture-Version-06.pdf> retrieved on Mar. 24, 2022; 6 pages.
Deterre et al. (2014). "Classification of commercial bitter orange essential oils (*Citrus aurantium* L.), based on a combination of chemical and sensory analyses of specific odor markers," Journal of Essential Oil Research 26 (4):254-262.
McLaughlin et al., U.S. Office Action dated Mar. 30, 2022, directed to U.S. Appl. No. 16/798,067; 20 pages.
Combined Search and Examination Report dated Nov. 22, 2021, directed to GB Application No. 2107172.5; 4 pages.
Combined Search and Examination Report dated Nov. 22, 2021, directed to GB Application No. 2107174.1; 4 pages.
Combined search and examination report dated Nov. 22, 2021, directed to GB Application No. 2107177.4; 5 pages.
International Search Report and Written Opinion dated Nov. 5, 2021, directed to International Application No. PCT/IB2021/056976; 15 pages.
Combined Search and Examination Report dated Apr. 28, 2020, directed to GB Application No. 2002466.7; 5 pages.
Combined Search and Examination Report dated Apr. 28, 2020, directed to GB Application No. 2002475.8; 7 pages.
Combined Search and Examination Report dated Apr. 28, 2020, directed to GB Application No. 2002479.0; 8 pages.
Combined Search and Examination Report dated Apr. 28, 2020, directed to GB Application No. 2002484.0; 7 pages.
International Search Report and Written Opinion dated Apr. 17, 2020, directed to International Application No. PCT/GB2020/050419; 15 pages.
International Search Report and Written Opinion dated Apr. 20, 2020, directed to International Application No. PCT/GB2020/050420; 13 pages.
International Search Report and Written Opinion dated Apr. 21, 2020, directed to International Application No. PCT/GB2020/050422; 14 pages.
International Search Report and Written Opinion dated Apr. 21, 2020, directed to International Application No. PCT/GB2020/050423; 14 pages.
McLaughlin et al., Office Action dated Apr. 12, 2021, directed to U.S. Appl. No. 16/797,927; 21 pages.
McLaughlin et al., Office Action dated Apr. 13, 2021, directed to U.S. Appl. No. 16/798,130; 29 pages.

(56) References Cited

OTHER PUBLICATIONS

McLaughlin et al., Office Action dated Dec. 7, 2020, directed to U.S. Appl. No. 17/008,318; 16 pages.
McLaughlin et al., Office Action dated Dec. 9, 2020, directed to U.S. Appl. No. 17/008,108; 22 pages.
McLaughlin et al., Office Action dated Feb. 10, 2021, directed to U.S. Appl. No. 16/797,934; 24 pages.
McLaughlin et al., Office Action dated May 12, 2021, directed to U.S. Appl. No. 16/797,934; 22 pages.
National Center for Biotechnology Information. (Apr. 28, 2006). "Compound Summary—Simethicone," located at https://pubchem.ncbi.nlm.nih.gov/compound/Simethicone (2 pages).
O'Connell (May 2005). "Sieve Use in the Pharmaceutical Industry," Pharmaceutical Technology Europe 17(5): 7 pages.
Syloid FG Silica (2015) "Syloid 244 FP silica: Formulation of viscous Simethicone in to chewable tablets," located at https://www.pharmaexcipients.com/wp-content/uploads/attachments/AP010_Syloid+244+FP-Formulation+of+Simethicone+into+chewable+tablets_Final.pdf?t=1458129627. (2 pages).
Zhou et al. (Aug. 2013). "Improving manufacturability of an ibuprofen powder blend by surface coating with silica nanoparticles," Powder Technology 249: 290-296.
Examination Report dated Feb. 6, 2023, directed to GB Application No. 2002466.7; 4 pages.
Examination Report dated Feb. 8, 2023, directed to GB Application No. 2107172.5; 3 pages.
Examination Report dated Feb. 14, 2023, directed to GB Application No. 2002475.8; 3 pages.
McLaughlin et al., U.S. Office Action dated Feb. 6, 2023, directed to U.S. Appl. No. 17/307,638; 17 pages.
Office Action dated Feb. 22, 2023, directed to IN Application No. 202127042578; 5 pages.
Office Action dated Feb. 27, 2023, directed to EP Application No. 20708584.6; 5 pages.
Bourgou et al. (2012). "Changes of Peel Essential Oil Composition of Four Tunisian Citrus during Fruit Maturation," The Scientific World Journal; Article ID 528593; 10 pages.
Jabri karoui et al. (2013). "Characterization of Bioactive Compounds in Tunisian Bitter Orange (*Citrus aurantium* L.) Peel and Juice and Determination of Their Antioxidant Activities," BioMed Research International; Article ID: 345415; 12 pages.
McLaughlin et al., U.S. Office Action dated Aug. 29, 2023, directed to US. Appl. No. 16/798,067; 16 pages.
Office Action dated Aug. 9, 2023, directed to MX Application No. MX/a/2021/009844; 5 pages.
Andrews. (2017). "How to Extract Oil from Orange Peels," downloaded from URL https://web.archive.org/web/20170603094953/https://www.wikihow.com/Extract-Oil-from-Orange-Peels retrieved on May 24, 2023; 5 pages.
Andrews. (2018) "How to Extract Oil from the Skin of Oranges," downloaded from https://www.weekand.com/healthy-living/article/extract-oil-skin-oranges-18009337.php retrieved on May 24, 2023; 4 pages.
Anonymous. (2013). "Making Orange Tincture," downloaded from https://boozyblog.wordpress.com/ 2013/08/05/making-orange-tincture/ retrieved on May 24, 2023; 7 pages.
Evonik-Gleriri Corp. "Aerosil® R972," located at https://glenncorp.com/shop/aerosil-r-972/, retrieved on May 16, 2023.(1 page).
Mclaughlin et al., U.S. Advisory Action dated Jun. 21, 2023, directed to U.S. Appl. No. 16/798,067; 5 pages.
McLaughlin et al., U.S. Office Action dated Jun. 16, 2023, directed to U.S. Appl. No. 17/529,827; 26 pages.
McLaughlin et al., U.S. Office Action dated Jun. 8, 2023, directed to U.S. Appl. No. 17/390,331; 11 pages.
Office Action dated Jul. 10, 2023, directed to RU Application No. 2021127592; 37 pages.
Office Action dated Jul. 11, 2023, directed to MX Application No. 2021-009845; 6 pages.
Office Action dated Jul. 12, 2023, directed to RU Application No. 2021127591; 25 pages.
Office Action dated Jul. 14, 2023, directed to RU Application No. 2021127588; 22 pages.
Office Action dated Jul. 28, 2023, directed to IN Application No. 202127042579; 8 pages.
Office Action dated Jun. 1, 2023, directed to GB Application No. 2107172.5; 1 page.
Office Action dated Jun. 23, 2023, directed to MX Application No. MX/a/2021/009679; 6 pages.
Office Action dated Jun. 27, 2023, directed to MX Application No. MX/a/2021/009681; 6 pages.
Office Action dated May 2, 2023, directed to IN Application No. 202127042581; 6 pages.
Office Action dated May 22, 2023, directed to CN Application No. 202080015446.5; 8 pages.
Office Action dated May 31, 2023, directed to GB Application No. 2002466.7; 1 pages.
Office Action dated May 31, 2023, directed to GB Application No. 2002475.8; 2 pages.
Office Action dated May 31, 2023, directed to IN Application No. 202127042580; 6 pages.
McLaughlin et al., U.S. Office Action dated Sep. 13, 2023, directed to U.S. Appl. No. 17/529,827; 15 pages.
Office Action dated Jul. 18, 2023, directed to TW Application No. 109105762; 14 pages.
Office Action dated Jul. 26, 2023, directed to TW Application No. 109105759; 12 pages.
Office Action dated Oct. 9, 2023, directed to MX Application No. MA/a/2021/009681; 9 pages.
Office Action dated Sep. 13, 2023, directed to MX Application No. MX/a/2021/009679; 10 pages.
Third Office Action dated Sep. 18, 2023, directed to CN Application No. 202080015446.5; 10 pages.
McLaughlin et al., U.S. Office Action dated Dec. 7, 2023, directed to U.S. Appl. No. 17/390,331; 6 pages.
Office Action dated Dec. 11, 2023, directed to RU Application No. 2021127590; 24 pages.
Office Action dated Dec. 6, 2023, directed to RU Application No. 2021127592; 17 pages.
Office Action dated Dec. 7, 2023, directed to RU Application No. 2021127591; 14 pages.
Office Action dated Nov. 17, 2023, directed to MX Application No. MX/a/2021/009844; 6 pages.
Office Action dated Nov. 3, 2023, directed to TW Application No. 109105770; 8 pages.
Office Action dated Sep. 28, 2023, directed to PH Application No. 1/2021/552022; 4 pages.
Extended European search report dated Dec. 18, 2023, directed to EP Application No. 23183926.7; 8 pages.
First Office Action dated Dec. 27, 2023, directed to CN Application No. 202080015572.0; 34 pages.
Notice of Reasons for Rejection dated Dec. 4, 2023, directed to JP Application No. 2021-549375; 11 pages.
Office Action dated Dec. 12, 2023, directed to RU Application No. 2021127588; 16 pages.
Office Action dated Nov. 1, 2023, directed MX Application No. MX/a/2021/009845; 11 pages.
Office Action dated Nov. 4, 2023, directed to CN Application No. 202080015635.2; 23 pages.
Office Action dated Nov. 7, 2023, directed to TW Application No. 109105773; 10 pages.
Office Action dated Nov. 8, 2023, directed to TW Application No. 109105762; 10 pages.
Office Action dated Nov. 9, 2023, directed to CN Application No. 202080015564.6; 28 pages.
Office Action dated Jul. 13, 2023, directed to RU Application No. 2021127590; 30 pages.
Chueshov et al. (2002). Industrial Drug Technology. vol. 2; pp. 352-355.
Pertsev et al. (1999). Pharmaceutical and biomedical aspects of drugs, vol. 1; pp. 253-254.

\* cited by examiner

MINIMIZING AGGLOMERATION, AERATION, AND PRESERVING THE COATING OF PHARMACEUTICAL COMPOSITIONS COMPRISING IBUPROFEN

CROSS REFERENCE TO RELATED APPLICATIONS

This application is a continuation of U.S. application Ser. No. 17/008,108, filed Aug. 31, 2020, which is a continuation of U.S. application Ser. No. 16/798,130, filed Feb. 21, 2020, which claims the priority of U.S. Provisional Application Nos. 62/809,307; 62/809,287; and 62/809,293, each filed Feb. 22, 2019, the entire contents of each of which are incorporated herein by reference.

FIELD

This relates to processes for coating Ibuprofen, and more particularly, to processes that minimize excess coating material to prevent agglomeration of the coated Ibuprofen in a lyophilized orally disintegrating dosage form during storage, processes that minimize aeration of pharmaceutical suspensions comprising Ibuprofen for improved dose weight accuracy whilst maintaining the integrity of the functional coat on the Ibuprofen, and processes that preserve the coating of coated Ibuprofen produced by solventless mixing processes and formulated to delay release of the Ibuprofen upon oral administration.

BACKGROUND

Pharmaceutical compositions typically include both an active pharmaceutical ingredient as well as one or more inactive ingredients. The active pharmaceutical ingredient (API) is biologically active and is designed to directly affect a patient's symptoms, diseases, disorders, and/or ailments. One example of an active pharmaceutical ingredient is Ibuprofen. The inactive ingredient(s) of a pharmaceutical composition, on the other hand, are pharmaceutically inert and can be used for various purposes including, but not limited to, improving long-term stabilization, filling or diluting a solid formulation, facilitating drug absorption, modifying viscosity of liquid formulations, enhancing solubility and/or aiding the manufacture of the pharmaceutical composition.

In addition, some inactive ingredients may be used to mask the taste of the API, such as Ibuprofen. Many APIs are known to exhibit unpleasant organoleptic properties if allowed to dissolve in the oral cavity, such as bitter taste, burning sensation and numbing. For example, some orally-administered pharmaceutical compositions are designed to disperse in the mouth to enable administration without water and are targeted to pediatric patients, geriatric patients, animal patients, and/or other types of patients that may have difficulties swallowing. For these types of orally-administered pharmaceutical compositions, an inactive ingredient may be used to form a "functional coating" to mask the taste of the API, or Ibuprofen.

For example, an inactive ingredient may be used to mask the taste of the API by wet coating or dry coating the API particle to produce a functional coating surrounding the API particle such that it prevents API release in the mouth. In wet particle coating, inactive ingredients (polymer and additives) are dissolved or dispersed in solvent or water to form a suspension or solution. This suspension or solution can then be sprayed onto the surface of the API particle to form a coating of film by evaporation of the solvent or water. Examples of technologies for wet particle coating include microencapsulation, fluid bed coating, spray drying, pan coating etc. In dry particle coating (also referred to as solventless coating), API particles are physically coated with fine particles of inactive ingredients (polymer and additives) to form particle composites. Examples of dry particle coating include hot melt coating, supercritical coating, impaction coating, electrostatic coating. API particles coated with a taste-masking inactive ingredient may provide a more pleasant experience for a patient having difficulties swallowing or having a sensitivity to taste that would otherwise lead to a negative patient experience and poor compliance.

Additionally, one type of pharmaceutical composition is an orally-disintegrating tablet (ODT). ODTs are pharmaceutical compositions targeted to pediatric patients, geriatric patients, animal patients, and/or other types of patients that may have difficulties swallowing.

To accurately dispense a pharmaceutical composition into a small, administrable form, a hydrophobic coated API particle can be placed in a matrix solution/suspension to form a pharmaceutical suspension. Mixing to form a pharmaceutical suspension allows for improved dosing accuracy. Oftentimes, this pharmaceutical suspension comprising the hydrophobic coated API particles can be dosed into molds, dried, and the molded article can then be transferred into a bottle, for example. However, this kind of handling of the pharmaceutical composition can increase risks such as damage and contamination.

Accordingly, many API suspensions today are dosed into preformed blister packs instead. Preformed blister packs eliminate one of the handling steps described above. Instead of dosing into a mold and then transferring the molded article to a bottle for packaging, preformed blister packs allow a manufacturer to dose the pharmaceutical suspension into a preformed blister pack that can be dried, then sealed and packaged. Thus, the preformed blister pack serves as both the mold and the package in which the pharmaceutical composition can be stored.

SUMMARY

Provided are methods for minimizing agglomeration of coating material for coated Ibuprofen produced using various mixing processes. Agglomeration of coating material can decrease the stability of the pharmaceutical product over time. For example, a pharmaceutical product's disintegration time may increase over time if it comprises agglomerated coating material. An increased disintegration times and/or a decreased dissolution rate implies an unstable pharmaceutical product. An unstable pharmaceutical product can lead to a shorter shelf life than desired. Accordingly, embodiments provided may help minimize agglomeration of coating material for coated Ibuprofen to improve the stability of the pharmaceutical product during storage and to increase its shelf life.

For example, methods described include removing excess coating material from the coated Ibuprofen to minimize the possibility of agglomeration of the coating material particles. Particularly, methods provided include sieving the coated Ibuprofen such that the final pharmaceutical product is adequately surrounded by dry matrix, minimizing any agglomeration of coating material particles upon storage. Pharmaceutical compositions described provide for a disintegration time and a dissolution rate that remain relatively stable over time.

Also provided are compositions and methods for preparing compositions that can minimize aeration of hydrophobic coated Ibuprofen in suspension. For example, hydrophobic coated Ibuprofen may be mixed into a matrix solution/suspension to form a pharmaceutical suspension to accurately dose into molds to form solid pharmaceutical compositions (e.g., article, tablet, etc.) for administering to a patient. However, the hydrophobicity of the coated Ibuprofen causes the coated Ibuprofen to resist dispersing into the solution/suspension. Consequently, this can cause air to become entrained with the pharmaceutical suspension, also known as aeration. Entrained air, or aeration of the pharmaceutical suspension, can cause phase separation of the coated Ibuprofen in the pharmaceutical suspension, causing a non-homogenous pharmaceutical suspension. Aeration and non-homogeneous pharmaceutical suspensions can lead to poor dose weight accuracy of the pharmaceutical suspension comprising the hydrophobic Ibuprofen dosed into preformed blister packs and poor content uniformity in the finished product (i.e., pharmaceutical composition).

Traditional mechanical means of anti-aeration and/or minimizing aeration have not been found to be successful due to the high viscosity of the pharmaceutical suspension. For example, minimizing aeration may be achieved by applying vacuum to a pharmaceutical suspension, but depending on the composition and further processing requirements this approach may not be suitable. In particular, applying a vacuum to the pharmaceutical suspension can cause the suspension to rise because the viscous suspension "holds onto" the entrained air. Volatile formulation components may also be lost during vacuum processing. Further, traditional anti-aerating agents, such as ethanol or simethicone emulsion are similarly ineffective at anti-aerating the suspension.

Accordingly, compositions and methods provided herein minimize the aeration of a pharmaceutical suspension comprising hydrophobic coated Ibuprofen to improve the homogeneity of the suspension and increase the dose weight accuracy. Specifically, embodiments provided can include matrix solutions/suspensions comprising chemical compounds comprising terpene and/or terpinol. In some embodiments, a matrix solution/suspension may comprise the terpene limonene. By introducing a terpene-comprising chemical compound such as limonene, the hydrophobic coated Ibuprofen may more readily incorporate into the matrix solution/suspension, minimizing the overall aeration of the pharmaceutical suspension.

Also provided herein are pharmaceutical compositions and methods for preparing pharmaceutical compositions that are formulated to preserve the functional coating of functionally-coated Ibuprofen during the manufacture process. Functionally-coated Ibuprofen are often mixed to form a pharmaceutical suspension. A pharmaceutical suspension allows for accurate dosing to form an administrable pharmaceutical product. Typically, shear forces required to incorporate the functionally-coated Ibuprofen into a pharmaceutical suspension can cause the functional coating to erode. Erosion of this coating can destroy or damage the properties of the functional coating. Accordingly, functionally-coated Ibuprofen with an eroded coating can experience an increased dissolution rate and decreased taste-masking properties when orally administered to a patient.

However, pharmaceutical compositions and methods for preparing pharmaceutical compositions provided herein include preserving the coating of functionally-coated Ibuprofen in the pharmaceutical suspension with hydrophobic fumed silica. Specifically, the hydrophobic fumed silica can provide a protective layer surrounding and/or embedded into the functionally-coated Ibuprofen particle. In some embodiments, solventless processes for producing functionally-coated Ibuprofen may produce Ibuprofen comprising a first coating. According to some embodiments, hydrophobic fumed silica can be added during the solventless mixing process to produce a second, protective coating surrounding and/or partially or fully embedded into the functionally-coated Ibuprofen.

Additionally, the second, protective coating may limit the interaction between the functionally-coated Ibuprofen and the matrix solution/suspension such that impact of the functionally-coated Ibuprofen on the performance characteristics of the matrix is minimized.

In some embodiments, a pharmaceutical composition comprises: 65-85% w/w Ibuprofen; 15-30% w/w coating material coating the Ibuprofen; and 3-15% w/w matrix surrounding the Ibuprofen. In some embodiments, the pharmaceutical composition comprises 50-400 mg Ibuprofen. In some embodiments, the coating material comprises a first coating material and a second coating material and the pharmaceutical composition comprises 10-30% w/w the first coating material and 0.5-10% w/w the second coating material. In some embodiments, the first coating material comprises a wax. In some embodiments, the second coating material comprises silica. In some embodiments, the pharmaceutical composition comprises 1-5% w/w anti-aerating agent. In some embodiments, the first coating material comprises one or more of carnauba wax, synthetic wax, or candelilla wax. In some embodiments, the matrix comprises a matrix former and a structure former. In some embodiments, the matrix former comprises one or more of a water soluble material, a water dispersible material, a polypeptide, a polysaccharide, a polyvinyl alcohol, a polyvinylpyrrolidone, and an acacia. In some embodiments, the matrix former comprises a polypeptide. In some embodiments, the polypeptide comprises gelatin. In some embodiments, the structure former comprises one or more of mannitol, dextrose, lactose, galactose, and cyclodextrin In some embodiments, the structure former comprises mannitol. In some embodiments, the pharmaceutical composition has a disintegration time of 4 seconds or less for at least one month under storage conditions of at least 25° C. and at least 60% relative humidity. In some embodiments, the pharmaceutical composition has a disintegration time of 4 seconds or less for at least two months under storage conditions of at least 25° C. and at least 60% relative humidity. In some embodiments, the pharmaceutical composition has a disintegration time of 3 seconds or less for at least two months under storage conditions of at least 25° C. and at least 60% relative humidity. In some embodiments, the pharmaceutical composition has a disintegration time of 4 seconds or less for at least one month under storage conditions of at least 30° C. and at least 65% relative humidity. In some embodiments, the pharmaceutical composition has a disintegration time of 4 seconds or less for at least two months under storage conditions of at least 30° C. and at least 65% relative humidity. In some embodiments, the pharmaceutical composition has a disintegration time of 4 seconds or less for at least one month under storage conditions of at least 40° C. and at least 75% relative humidity. In some embodiments, the pharmaceutical composition has a disintegration time of 4 seconds or less for at least two months under storage conditions of at least 40° C. and at least 75% relative humidity. In some embodiments, the pharmaceutical composition has a disintegration time of 4 seconds or less for at least three months under storage conditions of at least 25° C.

and at least 60% relative humidity. In some embodiments, the pharmaceutical composition has a disintegration time of 4 seconds or less for at least three months under storage conditions of at least 30° C. and at least 65% relative humidity. In some embodiments, the pharmaceutical composition has a disintegration time of 4 seconds or less for at least three months under storage conditions of at least 40° C. and at least 75% relative humidity. In some embodiments, the pharmaceutical composition has a disintegration time of 4 seconds or less for at least six months under storage conditions of at least 25° C. and at least 60% relative humidity. In some embodiments, the pharmaceutical composition has a disintegration time of 4 seconds or less for at least six months under storage conditions of at least 30° C. and at least 65% relative humidity. In some embodiments, the pharmaceutical composition has a disintegration time of 4 seconds or less for at least six months under storage conditions of at least 40° C. and at least 75% relative humidity. In some embodiments, the pharmaceutical composition has a dissolution test result of 10%, 5%, 3% or less after 5 minutes. In some embodiments, the matrix comprises a viscosity modifier. In some embodiments, the viscosity modifier comprises xanthan gum. In some embodiments, the anti-aerating agent comprises one or more of a terpene or a terpinol. In some embodiments, the anti-aerating agent comprises a liquid flavor. In some embodiments, wherein the anti-aerating agent comprises a liquid flavor comprising limonene. In some embodiments, the anti-aerating agent comprises one or more of orange flavor, lemon flavor, grapefruit flavor, lime flavor, strawberry flavor, or peppermint flavor. In some embodiments, the pharmaceutical composition comprises from 3-10% w/w matrix former. In some embodiments, the pharmaceutical composition comprises from 3-10% w/w structure former.

In some embodiments, a pharmaceutical composition can be prepared by a process comprising steps of: coating Ibuprofen with a first coating material to form coated Ibuprofen, wherein the first coating material comprises one or more deformable components; applying mechanical stress to the coated Ibuprofen to deform the one or more deformable components; coating the coated Ibuprofen with a second coating material comprising silica; applying mechanical stress to embed the second coating material onto the first coating material of the coated Ibuprofen; sieving the coated Ibuprofen to remove excess first coating material, wherein the excess first coating material comprises first coating material not bound to the coated Ibuprofen; forming a pharmaceutical suspension comprising the twice coated Ibuprofen and a matrix solution or suspension; dosing the pharmaceutical suspension into a mold; and freeze drying the dosed pharmaceutical suspension in the mold to form a pharmaceutical composition. In some embodiments, sieving the coated Ibuprofen comprises passing the coated Ibuprofen through a device comprising two or more sieves. In some embodiments, sieving the coated Ibuprofen comprises sieving the coated Ibuprofen to an average particle size of 75 µm or greater. In some embodiments, sieving the coated Ibuprofen comprises sieving the coated Ibuprofen to an average particle size of 200 µm or less. In some embodiments, the weight of dosed pharmaceutical suspension is within 10 percent of a target dose weight. In some embodiments, the weight of dosed pharmaceutical suspension has a consistency within 5 percent of a target dose weight. In some embodiments, the weight of dosed pharmaceutical suspension has a consistency within 2.5 percent of a target dose weight. In some embodiments, the weight of dosed pharmaceutical suspension has a consistency within 1 percent of a target dose weight. In some embodiments, mixing the coated Ibuprofen into a matrix solution or suspension comprises in-line mixing at 15-20° C. degrees Celsius. In some embodiments, the coated Ibuprofen experiences less than 40% loss in particle size within the first 2 hours after mixing into the solution matrix. In some embodiments, the coated Ibuprofen experiences less than 30% loss in particle size within the first 2 hours after mixing into the solution matrix. In some embodiments, the coated Ibuprofen experiences less than 20% loss in particle size within the first 2 hours after mixing into the solution matrix.

In some embodiments, a method of treating a patient comprises administering to a patient the pharmaceutical composition of any disclosed herein. In some embodiments, the patient is human.

In some embodiments, a method of preparing a pharmaceutical composition comprises: coating Ibuprofen with a first coating material to form coated Ibuprofen, wherein the first coating material comprises one or more deformable components; applying mechanical stress to the coated Ibuprofen to deform the one or more deformable components; coating the coated Ibuprofen with a second coating material comprising silica; applying mechanical stress to embed the second coating material onto the first coating material of the coated Ibuprofen; sieving the coated Ibuprofen to remove excess first coating material, wherein the excess first coating material comprises first coating material not bound to the coated Ibuprofen; forming a pharmaceutical suspension comprising the twice coated Ibuprofen and a matrix solution or suspension; dosing the pharmaceutical suspension into a mold; and freeze drying the dosed pharmaceutical suspension in the mold to form a pharmaceutical composition

BRIEF DESCRIPTION OF THE DRAWINGS

The invention will now be described, by way of example only, with reference to the accompanying drawings, in which.

DETAILED DESCRIPTION

Described herein are exemplary embodiments of methods for minimizing and/or preventing the agglomeration of the coating material of coated Ibuprofen, methods for preserving the coating of coated Ibuprofen, and methods of minimizing aeration of Ibuprofen in a pharmaceutical suspension. Also described are pharmaceutical compositions comprising Ibuprofen prepared by any one or more of the disclosed methods. Each of these methods and pharmaceutical compositions are described in detail below. Pharmaceutical compositions comprising Ibuprofen may be prepared using any combination of features from the preparation methods described below.

Figure 1A:
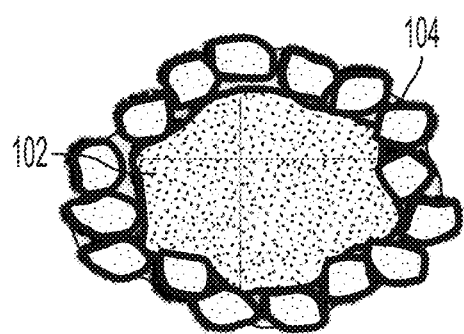
FIG. 1A shows an API particle coated with particles of a deformable coating material (i.e., a first coating layer) according to some embodiments.
Figure 1B:
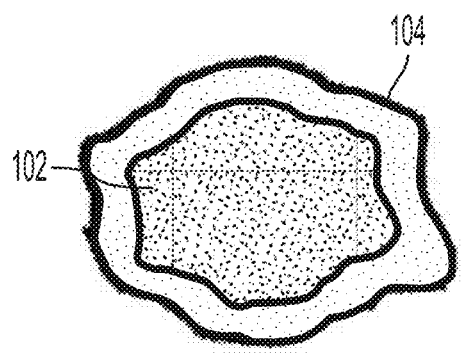
FIG. 1B shows an API particle coated with a continuous film layer of deformable coating material (i.e., a first coating layer) according to some embodiments.
Figure 1C:
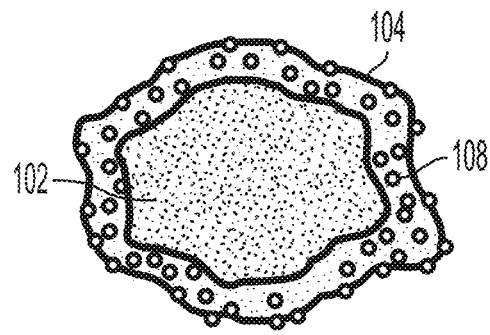
FIG. 1C shows an API particle coated with a continuous film layer of deformable coating material (i.e., a first coating layer) with particles of silica (i.e., a second coating layer) partially embedded and/or embedded on the surface of the first coating layer according to some embodiments.

FIGS. 1A, 1B, and 1C illustrate different phases of a coated API particle (e.g., Ibuprofen) according to some embodiments. In some embodiments, API particles can be combined with one or more coating materials to produce coated API. This coating may comprise materials including a water soluble and/or water swellable material and a water insoluble material (described in detail below).

Figure 2:
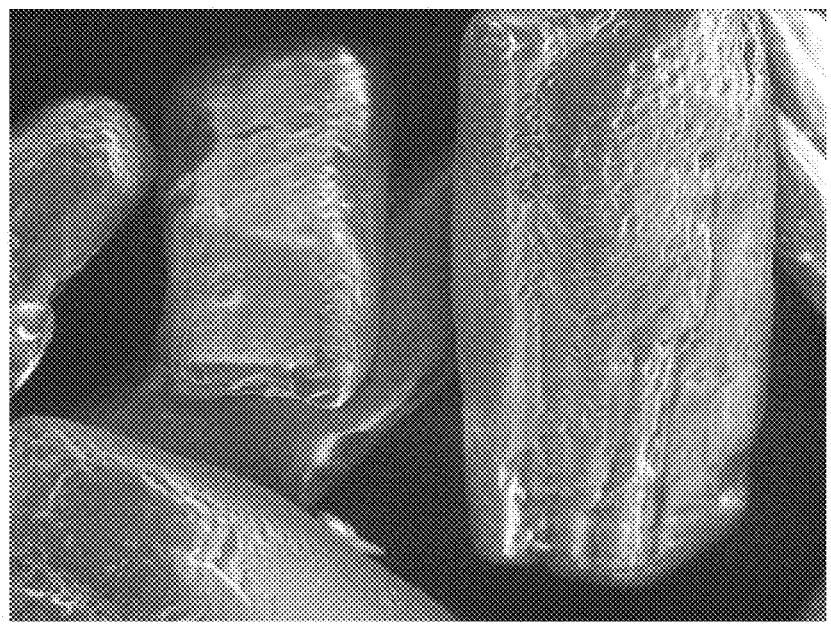
FIG. 2 shows a scanning electron microscope (SEM) image of an un-coated API particle according to some embodiments.

For example, FIG. 1A shows an API particle 102 surrounded by particles of a coating material 104. To achieve the coated API particle of FIG. 1A, the combined API (i.e., API particle 102) and one or more coating material(s) (i.e., coating material particles 104) may be exposed to mechanical and/or thermal energy to produce an ordered mixture of API particle 102 comprising a discrete layer of coating material particles 104 layering the surface of the API particle 102. API particle 102 of FIG. 1A is shown with a single layer of discrete particles of coating material(s). However, API particle 102 may have two or more discrete layers of coating particles. Additionally, FIG. 2 shows an SEM image of an un-coated API particle.

Figure 3:
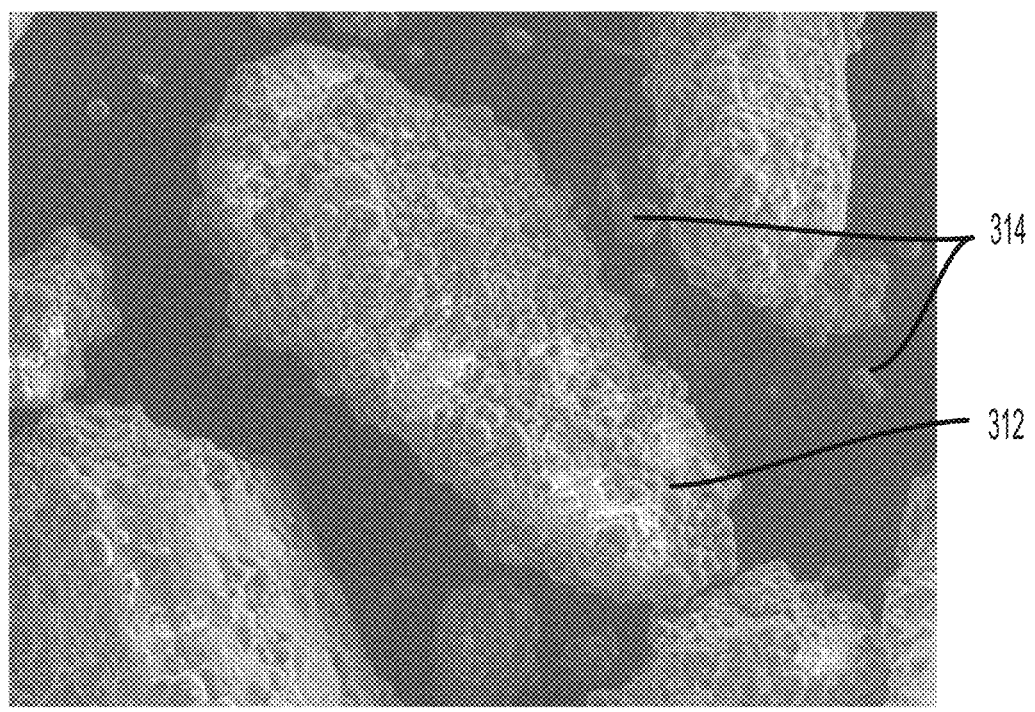
FIG. 3 shows an SEM image of a coated API particle, according to some embodiments.

FIG. 1B demonstrates API particle 102 surrounded by continuous, deformed film layer 104. Specifically, FIG. 1B shows that all of the coating material particles 104 may be deformable and may deform when subjected to mechanical stress and/or elevated temperature. Thus, because all the coating materials comprise deformable characteristics, the coating material 104 of FIG. 1B is a relatively smooth and continuous coating layer after exposure to mechanical and/or thermal energy. In some embodiments, API particle 102 may have two or more relatively smooth and continuous coating layers. "Continuous film" as used herein may be a layer surrounding an API particle formed by melting/softening or otherwise breaking down one or more deformable components of the individual coating material particles such that they comprise a single, continuous layer surrounding the API particle. FIG. 3 also provides an SEM image showing a coated API particle according to some embodiments.

In some embodiments, one or more of the coating materials may not be deformable but may be embedded in the deformable coating layer. Thus, the continuous film may comprise solid particles of the non-deformable material embedded within the deformed coating material. FIG. 1C shows that continuous film 104 may comprise solid non-deformable particles 108 of one or more non-deformable materials partially embedded and/or embedded within the deformed coating material of continuous film 104. This continuous film 104 of FIG. 1B or 1C can ensure a coating (for example, a coating that masks the taste of the API) and a delayed API release. In some embodiments, API particle 102 may have two or more continuous coating layers partially embedded and/or embedded with non-deformable coating material particles. FIG. 3 also provides an SEM image showing a functionally-coated API particle according to some embodiments.

As used herein, the terms "deformable", "deformable components", "deformable components of the coating material" and other related terms refer to one or more components of the water soluble, water swellable, and/or water insoluble materials that can be broken down when subjected to mechanical stress and/or elevated temperature.

In some embodiments, the coated API particles may comprise Ibuprofen. In some embodiments, the coated API particles or pharmaceutical composition may comprise from 30.0 to 90.0% w/w Ibuprofen. In some embodiments, the coated API particles or pharmaceutical composition may comprise from 40.0 to 85.0% w/w, from 50.0 to 80.0% w/w, or from 70.0 to 80.0% w/w Ibuprofen. In some embodiments, the coated API particles or pharmaceutical composition may comprise more than 40.0% w/w, more than 50.0% w/w, more than 60.0% w/w, more than 65% w/w, more than 70.0% w/w, more than 75.0% w/w, more than 80.0% w/w, or more than 85.0% w/w Ibuprofen. In some embodiments, the coated API particles or pharmaceutical composition may comprise less than 90.0% w/w, less than 85.0% w/w, less than 80.0% w/w, less than 75.0% w/w, less than 70.0% w/w, less than 60.0% w/w, less than 50.0% w/w, or less than 40.0% w/w Ibuprofen.

Coating 104 surrounding the API particle 102 may comprise materials including a water soluble and/or water swellable material and a water insoluble material. In some embodiments, this coating may coat an API particle (e.g., Ibuprofen) directly, or it may coat an API particle already comprising one or more coatings. In some embodiments, the ratio of coating material to API may be optimized to minimize excess coating material. For example, the coating material may comprise 5-85% w/w, 10-50%, 15-30% of the API and coating material mixture or pharmaceutical composition. In some embodiments, the coating material may comprise less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, or less than 10% of the API and coating material mixture or pharmaceutical composition. In some embodiments, the coating material may include more than 5%, more than 10%, more than 15%, more than 20%, more than 25%, more than 30%, more than 35%, more than 40%, more than 45%, more than 50%, more than 55%, more than 60%, more than 65%, more than 70%, or more than 75% of the API and coating material mixture or pharmaceutical composition. In some embodiments, the coating material percentage may include two or more layers of coating material.

The water swellable material of the coating material may be a particle comprising a median particle size of about 0.5 µm to about 20 µm or about 1 µm to about 10 µm. In some embodiments, the water swellable material may be approximately ten times smaller than that of the Ibuprofen to enable ordered mixing and coating. The water swellable material can swell upon absorption of water such that a diameter of the water swellable particle increases at least by about 120-600%. The coating material or pharmaceutical composition may comprise from 0 to 8% w/w or from 0.1 to 0.9% w/w water swellable materials. In some embodiments, the coating material or pharmaceutical composition may comprise from 0.5 to 6.0% w/w, from 1.0 to 4.0% w/w, from 1.5 to 3.5% w/w, or from 2.0 to 3.0% w/w water swellable materials. In some embodiments, the coating material or pharmaceutical composition may comprise less than 8.0% w/w, less than 6.0% w/w, less than 4.0% w/w, less than 2.0% w/w, less than 1.0% w/w, or less than 0.5% w/w water swellable materials. In some embodiments, the coating material or pharmaceutical composition may comprise greater than 0.1% w/w, greater than 0.5% w/w, greater than 1.0% w/w, greater than 2.0% w/w, greater than 3.0 w/w %, greater than 5.0% w/w, or greater than 6.0% w/w water swellable materials. The water swellable material of the coating material may be deformable under mechanical stress and/or elevated temperature (described in detail below). The water swellable material may be any one or more of crospovidone, croscarmellose, sodium starch glycolate, or any other suitable disintegrant used in the pharmaceutical industry as an additive or blend made for tableting.

The water soluble material of the coating material may also be a particle comprising a median particle size of about 0.5 µm to about 20 µm or about 1 µm to about 10 µm. In some embodiments, the water soluble material may be approximately ten times smaller than that of the Ibuprofen to enable ordered mixing and coating. The water soluble material may have a water solubility of at least about 50 mg/ml in water at a neutral pH and at 20° C. Further, the water soluble material can have an intrinsic dissolution rate of about 3-60 µg/m²s. The water soluble material of the coating material may be deformable under mechanical energy and/or thermal energy. The coating material or pharmaceutical composition may comprise from 0 to 35% w/w water soluble materials. In some embodiments, the coating material or pharmaceutical composition may comprise from 0.5 to 25% w/w, from 1.0 to 15% w/w, from 1.5 to 10% w/w, or from 2.0 to 3.0% w/w water soluble materials. In some embodiments, the coating material or pharmaceutical composition may comprise less than 35% w/w, less than 30% w/w, less than 25% w/w, less than 20% w/w, less than 15% w/w, less than 10% w/w, less than 5.0% w/w, less than 4.5% w/w, less than 4.0% w/w, less than 3.5% w/w, less than 3.0% w/w, less than 2.5% w/w, less than 2.0% w/w, less than 1.5% w/w, less than 1.0% w/w, or less than 0.5% w/w water soluble materials. In some embodiments, the coating material or pharmaceutical composition may comprise more than 0.1% w/w, more than 0.5% w/w, more than 1.0% w/w, more than 1.5% w/w, more than 2.0% w/w, more than 2.5% w/w, more than 3.0% w/w, more than 4.0% w/w, more than 5.0% w/w, more than 8.0% w/w, more than 10% w/w, more than 15% w/w, more than 20% w/w, more than 25% w/w, or more than 30% w/w water soluble materials. The water soluble material may be one or more of sucrose, mannitol, sorbitol, polyvinylpyrrolidone, hydroxypropylcellulose, lactose, poly-(ethylene oxide), and any other suitable micronizable materials or polyols.

In addition to an intrinsic dissolution rate of 3-60 µg/m²s discussed above, processes provided can permit the use of water soluble and/or water swellable materials having a higher intrinsic dissolution rate of about 60-300 µg/m²s as well. However, Ibuprofen with coating materials having a higher intrinsic dissolution rate should be dry coated with hydrophobic silica. Dry coating Ibuprofen wherein the coating comprises water soluble and/or water swellable materials having higher intrinsic dissolution rates can increase the disintegration time of the ibuprofen, such that they are incapable of masking of the Ibuprofen's taste effectively. Accordingly, dry coating the Ibuprofen with silica as a second coating material to slow the dissolution rate can improve the in-vivo taste-masking performance of the coating. The coated Ibuprofen may comprise from 0.5 to 35% w/w silica. In some embodiments, the coated Ibuprofen or pharmaceutical composition can comprise from 0.5 to 20% w/w, from 0.5 to 10% w/w, or from 0.5 to 5% w/w hydrophobic fumed silica. In some embodiments, the coated Ibuprofen or pharmaceutical composition can comprise more than 0.5% w/w, more than 1.0% w/w, more than 1.5% w/w, more than 2.0% w/w, more than 2.5% w/w, more than 3.0% w/w, more than 4.0% w/w, more than 5.0% w/w, more than 10% w/w, more than 15% w/w, more than 20% w/w, more than 25% w/w, or more than 30% w/w hydrophobic fumed silica. In some embodiments, the coated Ibuprofen or pharmaceutical composition can comprise less than 35% w/w, less than 25% w/w, less than 15% w/w, less than 10% w/w, less than 5.0% w/w, less than 4.0% w/w, less than 3.5% w/w, less than 3.0% w/w, less than 2.5% w/w, less than 2.0% w/w, less than 1.5% w/w, less than 1.0% w/w, or less than 1.0% w/w hydrophobic fumed silica. Examples of silica that may be used include, but are not limited to, Aerosil R972 silica (Degussa), CAB-O-SIL EH-5 silica (Cabot), OX-50 silica (Degussa), COSM055 (Catalyst & Chemical Ind. Co. Ltd (Japan)), P-500 hydrophilic silica (Catalyst & Chemical Ind. Co. Ltd (Japan)), and TS5 silica (Cabot). Further, suitable devices that may be used to dry coat with silica include, but are not limited to, Comil (U3 Quadro Comil of Quadro Pennsylvania, U.S.), LabRAM (Resodyne Minnesota, U.S.), Magnetically Assisted Impact Coater (MAIC, Aveka Minnesota, U.S.), and Fluid Energy Mill (FEM, Qualification Micronizer of Sturtevant Massachusetts U.S.).

A pharmaceutical composition may be prepared by dosing the pharmaceutical suspension into preformed blister packs. In some embodiments, a freeze-dried orally disintegrating tablet may be prepared by dosing the suspension into blister packs. In some embodiments, dosing pumps pump by volume, but the process is controlled by weight. Thus, to ensure content uniformity from one dosage form to the next, the dosing process may be controlled such that the volume-to-weight percentage of dosed suspension is consistent. For example, a volume-to-weight percentage may be consistent within 10 percent, within 8 percent, within 6 percent, within 5 percent, within 4 percent, within 3 percent, within 2 percent, within 1.5 percent, within 1 percent, within 0.5 percent, or within 0.25 percent. In some embodiments, the weight of the dosed pharmaceutical suspension is within 10 percent, within 8 percent, within 6 percent, within 5 percent, within 4 percent, within 2.5 percent, within 2 percent, within 1.5 percent, within 1 percent, within 0.5 percent, or within 0.25 percent of a target weight. Additionally, the viscosity of the pharmaceutical suspension should be kept low enough for ease of dosing. As described above, a high viscosity of the pharmaceutical suspension can case pump seizures during dosing.

The water insoluble material of the coating materials may also be a particle comprising an average particle size less than that of the Ibuprofen. For example, the water insoluble material(s) may comprise an average particle size from about 1-20 µm, about 1-12 µm, about 2-10 µm, about 5-12 µm, or about 5-6 µm. In some embodiments, the water insoluble material may be approximately ten times smaller than that of the Ibuprofen to enable ordered mixing and coating. The water insoluble material of the coating material may be deformable under mechanical stress and/or elevated temperature. The coating material or pharmaceutical composition may comprise from 5 to 70% w/w, from 10 to 60% w/w, from 10 to 50% w/w, from 10 to 40% w/w, from 10 to 35% w/w, or from 15 to 30% w/w water insoluble materials. In some embodiments, the coating material or pharmaceutical composition may comprise more than 5% w/w, more than 10% w/w, more than 15% w/w, more than 20% w/w, more than 25% w/w, more than 30% w/w, more than 35% w/w, or more than 40% w/w water insoluble materials. In some embodiments, the coating material or pharmaceutical composition may comprise less than 70% w/w, less than 60% w/w, less than 50% w/w, less than 45% w/w, less than 40% w/w, less than 35% w/w, or less than 30% w/w water insoluble materials. Examples of suitable water insoluble materials include, but are not limited to ethylcellulose, polyethylene, polypropylene, polytetrafluoroethylene, carnauba wax, candelilla wax, castor wax, polyamide wax and/or synthetic wax.

In some embodiments, mechanical and/or thermal energy may be used to deform the one or more water insoluble materials, water swellable materials, and/or water insoluble materials. For example, mechanical stress can be applied to the functionally-coated Ibuprofen using a PharmaRAM II acoustic mixer, a RAM 5 Pharma mixer, or a RAM 55 Pharma mixer (Resodyn Mixers). The coated Ibuprofen may be exposed to up to 100 times the force of gravity (100G acceleration) during this acoustic mixing process. These high forces cause particle-particle collisions that generate energy in the form of heat, which may be used to deform the one or more water insoluble materials, water swellable materials, and/or water insoluble materials onto the API.

However, the coating process described above can also generate "loose", or "free" coating material particles. FIG. 2 is an SEM image of an uncoated API particle. FIG. 3 is an SEM image of coated API particle 312. "Loose" or "free" coating material particles 314 are not bound to coated API particle 312.

Once sieved, the coated Ibuprofen can be mixed into a matrix solution/suspension to form a pharmaceutical suspension (e.g., coated Ibuprofen plus matrix solution/suspension) and dosed by weight into pockets of preformed blister packs to form aliquots of pharmaceutical suspension. Once dosed, the blister packs with aliquots pharmaceutical suspension are frozen under sub-zero conditions. The frozen aliquots of dosed pharmaceutical suspension is held frozen until it is ready for freeze drying during which the solvent of the pharmaceutical suspension is removed to form the pharmaceutical composition.

The matrix solution/suspension may include a matrix former, a structure former, and a solvent. For example, the matrix former may include any water soluble or water dispersable material that is pharmacologically acceptable or inert to the functionally-coated Ibuprofen. In some embodiments, the matrix former may be a polypeptide such as gelatin. The gelatin may be at least partially hydrolyzed (by heating in water). Other suitable matrix former materials include, but are not limited to, polysaccharides such as hydrolyzed dextran, dextrin, and alginates, polyvinyl alcohol, polyvinylpyrrolidone, and/or acacia. In some embodiments, the amount of matrix in a pharmaceutical composition (e.g., an orally disintegrating tablet) may be 1-30% w/w. In some embodiments, the amount of matrix may be less than 30% w/w, less than 25% w/w, less than 20% w/w, less than 15% w/w, less than 10% w/w, less than 5% w/w, or less than 3% w/w. In some embodiments, the amount of matrix may be more than 1% w/w, more than 3% w/w, more than 5% w/w, more than 10% w/w, more than 15% w/w, more than 20% w/w, or more than 25% w/w.

In some embodiments, the amount of matrix former in a matrix solution/suspension or pharmaceutical suspension can be from about 0.1 to 10% w/w. In some embodiments, the amount of matrix former in the matrix solution/suspension or pharmaceutical suspension may include from 1.0 to 8.0% w/w or from 2.0 to 5.0% w/w. In some embodiments, the amount of matrix former in the matrix solution/suspension or pharmaceutical suspension may include more than 0.1% w/w, more than 0.5% w/w, more than 1.0% w/w, more than 2.0% w/w, more than 3.0% w/w, more than 4.0% w/w, more than 4.5% w/w, more than 5.0% w/w, or more than 8.0% w/w. In some embodiments, the amount of matrix former in the matrix solution/suspension or pharmaceutical suspension may include less than 10% w/w, less than 8.0% w/w, less than 6.0% w/w, less than 5.0% w/w, less than 4.0% w/w, less than 3.0% w/w, less than 2.5% w/w, less than 2.0% w/w, less than 1.5% w/w, or less than 1.0% w/w. In some embodiments, the amount of matrix former in a pharmaceutical composition can be about 3-15% w/w, about 4-10% w/w, or about 4-7% w/w. In some embodiments, the amount of matrix former in the pharmaceutical composition may include more than 0.1% w/w, more than 0.5% w/w, more than 1.0% w/w, more than 2.0% w/w, more than 3.0% w/w, more than 4.0% w/w, more than 5.0% w/w, more than 6.0% w/w, more than 7.0% w/w, more than 8.0% w/w, more than 9.0% w/w, more than 10.0% w/w, more than 11.0% w/w, more than 12.0% w/w, more than 13.0% w/w, or more than 14.0% w/w. In some embodiments, the amount of matrix former in the pharmaceutical composition may include less than 15% w/w, less than 14.0% w/w, less than 13.0% w/w, less than 12.0% w/w, less than 10.0% w/w, less than 9.0% w/w, less than 8% w/w, less than 7% w/w, less than 6% w/w, less than 5% w/w, or less than 4.0% w/w.

A structure former, or bulking agent, of the matrix may include a sugar. For example, suitable structure formers include, but are not limited to, mannitol, dextrose, lactose, galactose, glycine, cyclodextrin, or combinations thereof. The structure former can be used in freeze drying as a bulking agent as it crystallizes to provide structural robustness to the freeze-dried dosage form. In some embodiments, the amount of structure former in the matrix solution/suspension can be from about 0.1 to 10% w/w. In some embodiments, the amount of structure former in the matrix solution/suspension or pharmaceutical suspension may include from 1.0 to 8.0% w/w or from 1.5 to 5.0% w/w. In some embodiments, the amount of structure former in the matrix solution/suspension or pharmaceutical suspension may include more than 0.1% w/w, more than 0.5% w/w, more than 1.0% w/w, more than 2.0% w/w, more than 3.0% w/w, more than 4.0% w/w, more than 4.0% w/w, more than 5.0% w/w, or more than 8.0% w/w. In some embodiments, the amount of structure former in the matrix solution/suspension or pharmaceutical suspension may include less than 10% w/w, less than 8.0% w/w, less than 6.0% w/w, less than 5.0% w/w, less than 4.0% w/w, less than 3.0% w/w, less than 2.5% w/w, less than 2.0% w/w, less than 1.5% w/w, or less than 1.0% w/w. In some embodiments, the amount of structure former in a pharmaceutical composition can be about 3-15% w/w, about 4-10% w/w, or about 4-7% w/w. In some embodiments, the amount of structure former in the pharmaceutical composition may include more than 0.1% w/w, more than 0.5% w/w, more than 1.0% w/w, more than 2.0% w/w, more than 3.0% w/w, more than 4.0% w/w, more than 5.0% w/w, more than 6.0% w/w, more than 7.0% w/w, more than 8.0% w/w, more than 9.0% w/w, more than 10.0% w/w, more than 11.0% w/w, more than 12.0% w/w, more than 13.0% w/w, or more than 14.0% w/w. In some embodiments, the amount of structure former in the pharmaceutical composition may include less than 15% w/w, less than 14.0% w/w, less than 13.0% w/w, less than 12.0% w/w, less than 10.0% w/w, less than 9.0% w/w, less than 8% w/w, less than 7% w/w, less than 6% w/w, less than 5% w/w, or less than 4.0% w/w.

In some embodiments, a matrix solution/suspension and pharmaceutical suspension may include a viscosity modifier. For example, a viscosity modifier according to embodiments provided herein may include vegetable gums such as xanthan gum, alginin, guar gum, or locust bean gum, proteins such as collagen or gelatin, sugars such as agar, carboxymethyl cellulose, pectin, or carrageenan, starches such as arrowroot, cornstarch, katakuri starch, potato starch, sago, or tapioca, and/or other suitable viscosity modifiers. In some embodiments, the amount of viscosity modifier in the matrix solution/suspension, pharmaceutical suspension, or the pharmaceutical composition may be from 0 to 0.2% w/w or from 0.01 to 0.1% w/w. In some embodiments, the amount of viscosity modifier in the matrix solution/suspension, pharmaceutical suspension, or the pharmaceutical composition may be greater than 0.01% w/w, greater than 0.03% w/w, greater than 0.05% w/w, greater than 0.07% w/w, greater than 0.1% w/w, greater than 0.12% w/w, greater than 0.15% w/w, or greater than 0.17% w/w. In some embodiment, the amount of viscosity modifier in the matrix solution/suspension, pharmaceutical suspension, or the pharmaceutical composition may be less than 0.2% w/w, less than 0.18% w/w, less than 0.15% w/w, less than 0.12% w/w, less than 0.1% w/w, less than 0.08% w/w, less than 0.06% w/w, or less than 0.03% w/w.

The solvent of the matrix solution/suspension and pharmaceutical suspension may be water, but the suspension solution may include a cosolvent as well. In some embodiments, the solvent can be ethanol, alcohol, isopropanol, other lower alkanols, water (e.g., purified water), or combinations thereof. For example, a suitable solvent and/or cosolvent may be an alcohol, such as tert-butyl alcohol. In some embodiments, the balance remaining of the pharmaceutical suspension is the solvent (i.e., Q.S. 100%).

The matrix solution/suspension and pharmaceutical suspension may also contain additional pharmaceutically acceptable agents or excipients. Such additional pharmaceutically acceptable agents or excipients include, without limitation, sugars, inorganic salts, such as sodium chloride and aluminum silicates, modified starches, preservatives, antioxidants, viscosity enhancers, coloring agents, flavoring agents, pH modifiers, sweeteners, taste-masking agents, and combinations thereof. Suitable coloring agents can include red, black and yellow iron oxides and FD & C dyes such as FD & C Blue No. 2 and FD & C Red No. 40, and combinations thereof. Suitable flavoring agents can include mint, raspberry, licorice, orange, lemon, grapefruit, caramel, vanilla, cherry and grape flavors and combinations of these. Suitable pH modifiers can include citric acid, tartaric acid, phosphoric acid, hydrochloric acid, maleic acid, sodium hydroxide (e.g., 3% w/w sodium hydroxide solution), and combinations thereof. Suitable sweeteners can include aspartame, acesulfame K and thaumatin, and combinations thereof. Suitable taste-masking agents can include sodium bicarbonate, ion-exchange resins, cyclodextrin inclusion compounds, adsorbates or microencapsulated actives, and combinations thereof. One of ordinary skill in the art can readily determine suitable amounts of these various additional excipients if desired.

Minimizing and/or Preventing the Agglomeration of the Coating Material of Coated Ibuprofen Described below are methods for preparing pharmaceutical compositions comprising Ibuprofen that minimize the amount of excess coating material and/or the amount of agglomeration of excess coating material on storage.

Methods according to some embodiments include removing excess coating material particles to minimize and/or to prevent agglomeration of coating material in a pharmaceutical product. In some embodiments, methods may include sieving the raw Ibuprofen and/or the coated Ibuprofen. Specifically, methods provided may include sieving the Ibuprofen and/or the coated Ibuprofen to remove any undesired particles, such as excess coating material particles. Sieving processes according to embodiments disclosed may help prevent and/or minimize the potential of coating material agglomeration that can adversely affect a disintegration time and/or a dissolution rate of the final product. Methods may also include optimizing the coating and/or dosing ratios of the process.

Methods for minimizing and or preventing agglomeration of coating material particles according to embodiments described herein may be applied to dry, solventless mixing processes for coating Ibuprofen. Accordingly, methods provided are described below in context of one or more dry, solventless mixing processes for coating Ibuprofen. However, other variations of coating/encapsulating processes may be used as well. For example, sugar coating, film coating, other variations of microencapsulation, compression coating, other variations of dry coating, melting coating, dip coating, rotary die coating, electrostatic coating, and/or other suitable types of coating may be used.

Generally, a solventless mixing process for coating Ibuprofen includes mixing coating materials with Ibuprofen to produce coated Ibuprofen. The coated Ibuprofen are then stressed mechanically and/or thermally to deform the deformable coating material, creating a continuous film surrounding the Ibuprofen. The coated Ibuprofen are then mixed with a matrix solution/suspension to form the pharmaceutical suspension. The pharmaceutical suspension comprising the coated Ibuprofen can be dosed into preformed molds, such as blister packs, and further treated to produce a dispensable pharmaceutical composition (e.g., a lyophilizate, a wafer, a tablet, etc.).

However, when the final product (i.e., pharmaceutical composition) is stored, any excess coating material particles not bound to coated Ibuprofen can agglomerate. The amount and/or severity of agglomeration may increase over time. Agglomeration of excess coating material can increase the disintegration times and/or decrease the dissolution rate of the pharmaceutical product and adversely affect any functional properties of the coating material. An increased disintegration time may also cause unacceptable dispersion and mouthfeel characteristics in vivo.

Accordingly, it has been discovered that by sieving the coated Ibuprofen, excess coating material can be removed, thus minimizing the amount of agglomeration of excess coating material upon storage. Further, some embodiments include optimizing the coating ratio (amount of coating materials to the amount of uncoated Ibuprofen) and optimizing the dosing ratio (amount of coated Ibuprofen to the aqueous solution matrix comprising all the other inactive ingredients) can also minimize the agglomeration of excess coating material particles.

Embodiments provided herein can be applied to coated Ibuprofen produced using dry, solventless processes. Some mixing processes according to embodiments described herein include coating Ibuprofen with a taste-masking coating. Such coatings can control the disintegration time and/or the dissolution rate of an orodispersible pharmaceutical composition such that the release of the Ibuprofen upon oral administration is delayed or significantly reduced during the first few minutes when it is in the mouth, yet a satisfactory amount of the Ibuprofen is released within 30 minutes from oral administration post swallowing. (For example, a satisfactory amount of Ibuprofen may be 90% of the Ibuprofen amount which would be released without the coating). U.S. Pat. No. 9,107,851 (the '851 patent) is directed to an example dry, solventless process for coating pharmaceutical ingredients, the entirety of which is incorporated herein.

However, other variations of coating/encapsulating processes may be used as well. For example, sugar coating, film coating, other variations of microencapsulation, compression coating, other variations of dry coating, melting coating, dip coating, rotary die coating, electrostatic coating, and/or other suitable types of coating may be used.

Additionally, specific data as provided herein is related to disintegration times. However, disintegration time is inversely related to dissolution rates. Thus, the data inherently provides information on dissolution rates as well. Disintegration time may be measured according to methods set forth by the United States Pharmacopeia (Disintegration 701). In some embodiments, the disintegration time may be from 2-30 seconds or 5-20 seconds. In some embodiments, the disintegration time may be less than 30 seconds, less than 25 seconds, less than 20 seconds, less than 15 seconds, less than 10 seconds, or less than 5 seconds. In some embodiments, the disintegration time may be greater than 2 seconds, greater than 5 seconds, greater than 10 seconds, greater than 15 seconds, greater than 20 seconds, or greater than 25 seconds. Similarly, dissolution rate may also be tested according to methods set forth by the United States Pharmacopeia (Dissolution 711).

In some embodiments, raw Ibuprofen may be sieved prior to the coating process to achieve a narrower particle size range. For example, the raw Ibuprofen may be sieved to remove oversized particles and/or to remove undersized particles. In some embodiments, more than one mesh can be used to remove certain particles. For example, a sieving device may comprise a series of two or more meshes to remove particles of a certain size according to the size of the mesh(es). The sieve can incorporate a vacuum transfer system to transport the particles through the series of meshes of the device. Additionally, ultrasonic probes may be incorporated into the sieving device to improve material flow and minimize blinding of the mesh during processing.

In some embodiments, the raw Ibuprofen can be sieved using a mesh size from 30 µm to 500 µm, from 50 µm to 450 µm, from 100 µm to 400 µm, from 150 µm to 350 µm, or from 200 µm to 300 µm. In some embodiments, the raw Ibuprofen can be sieved using a mesh size less than 500 µm, less than 450 µm, less than 400 µm, less than 350 µm, less than 300 µm, less than 250 µm, less than 200 µm, less than 150, or less than 100 µm. In some embodiments, the raw Ibuprofen can be sieved using a mesh size greater than 30 µm, greater than 50 µm, greater than 100 µm, greater than 150 µm, greater than 200 µm, greater than 250 µm, greater than 300 µm, greater than 350 µm, or greater than 400 µm.

Once the Ibuprofen have been coated by the coating material to produce coated Ibuprofen, the coated Ibuprofen may be sieved to remove excess coating material and residual fine Ibuprofen, either uncoated, partially coated or coated. Excess coating material may include any coating material particles not bound to a coated Ibuprofen. Upon storage of the final pharmaceutical product, any excess coating material can agglomerate. For example, fusion may occur between excess coating particles and coating particles that are already bound to an Ibuprofen, preventing ingress of media that would otherwise aid in disintegration of the unit or tablet or dissolution of the coated Ibuprofen. Accordingly, agglomeration of excess coating material can cause increased disintegration times and/or decreased dissolution rates upon administration.

However, it has been determined that methods of sieving excess coating material from the coated Ibuprofen can minimize agglomeration of the coating material and maintain the initial disintegration time and/or dissolution rate of the final product. The sieving process can be either batch or continuous. Additionally, this sieving process may be performed in addition to or in lieu of the sieving process performed on raw Ibuprofen, described above. In some embodiments, the sieving process parameters may be different between the uncoated, raw Ibuprofen and the coated Ibuprofen.

In some embodiments, coated Ibuprofen may be sieved to remove coating material particles having an average particle size less than a desired average coated Ibuprofen particle size. In some embodiments, more than one mesh can be used to remove certain particles. For example, a sieving device may comprise a series of two or more meshes to remove particles of a certain size according to the size of the mesh(es). The sieve can incorporate a vacuum transfer system to deliver the particles to the series of meshes of the device. Additionally, ultrasonic probes may be incorporated into the sieving device to improve material flow and minimize blinding of the mesh during processing. A flow aid (e.g., silica) may be included to promote movement through the sieve. For example, the coating material used to coat the Ibuprofen may comprise a flow aid. Conversely, raw Ibuprofen may not be cohesive and not require the assistance of a flow aid during sieving. The sieving process may be a batch process or a continuous process.

In some embodiments, the raw Ibuprofen can be sieved using a mesh size from 30 µm to 500 µm, from 50 µm to 450 µm, from 100 µm to 400 µm, from 150 µm to 350 µm, or from 200 µm to 300 µm. In some embodiments, the raw Ibuprofen can be sieved using a mesh size less than 500 µm, less than 450 µm, less than 400 µm, less than 350 µm, less than 300 µm, less than 250 µm, less than 200 µm, less than 150, or less than 100 µm. In some embodiments, the raw Ibuprofen can be sieved using a mesh size greater than 30 µm, greater than 50 µm, greater than 100 µm, greater than 150 µm, greater than 200 µm, greater than 250 µm, greater than 300 µm, greater than 350 µm, or greater than 400 µm.

The coating ratio (i.e., the amount of coating materials to the amount of uncoated Ibuprofen) may be optimized to minimize and/or prevent the agglomeration of the excess coating materials. For example, in some embodiments, the coating ratio can ranges from 5-85% or 10-50% w/w coating materials to 15-95% or 50-90% w/w uncoated Ibuprofen. In some embodiments, the amount of coating materials may be less than 80% w/w, less than 70% w/w, less than 60% w/w, less than 50% w/w, less than 40% w/w, less than 30% w/w, less than 20% w/w, or less than 10% w/w. In some embodiments, the amount of coating materials may be more than 5% w/w, more than 10% w/w, more than 20% w/w, more than 30% w/w, more than 40% w/w, more than 50% w/w, more than 60% w/w, or more than 70% w/w. In some embodiments, the amount of uncoated Ibuprofen may be less than 95% w/w, less than 85% w/w, less than 75% w/w, less than 65% w/w, less than 55% w/w, less than 45% w/w, less than 35% w/w, or less than 25% w/w. In some embodiments, the amount of uncoated API may be more than 20% w/w, more than 30% w/w, more than 40% w/w, more than 50% w/w, more than 60% w/w, more than 70% w/w, more than 80% w/w, or more than 90% w/w.

The dosing ratio (i.e., the amount of coated Ibuprofen to the amount of matrix solution/suspension comprising all the inactive ingredients) may be optimized to minimize and/or prevent the agglomeration of the excess coating materials. For example, in some embodiments, the dosing ratio can range from 5-60% w/w coated Ibuprofen to 40-95% w/w matrix solution/suspension. In some embodiments, the dosing ratio may include less than 60% w/w, less than 50% w/w, less than 40% w/w, less than 30% w/w, less than 20% w/w, or less than 10% w/w coated Ibuprofen. In some embodiments, the dosing ratio may include more than 5% w/w, more than 10% w/w, more than 20% w/w, more than 30% w/w, more than 40% w/w, or more than 50% w/w coated Ibuprofen. In some embodiments, the dosing ratio may include less than 95% w/w, less than 90% w/w, less than 80% w/w, less than 70% w/w, less than 60% w/w, or less than 50% w/w matrix solution/suspension. In some embodiments, the dosing ration may include more than 40% w/w, more than 50% w/w, more than 60% w/w, more than 70% w/w, more than 80% w/w, or more than 90% w/w matrix solution/suspension.

Preserving Functionally-Coated Ibuprofen Produced by a Dry, Solventless Mixing Process and Mixed in a Suspension Pharmaceutical compositions and methods for preparing pharmaceutical compositions provided herein may include adding hydrophobic fumed silica during the coating process to provide a protective layer surrounding and/or partially or fully embedded into a functional (or "first coating") of the functionally-coated Ibuprofen. The addition of this hydrophobic fumed silica layer (or "second layer") can provide a protective layer to a first coating layer of functionally-coated Ibuprofen and can minimize erosion of the first coating layer from shear forces necessary to mix the functionally-coated Ibuprofen into pharmaceutical suspension.

Generally, a solventless mixing process for coating Ibuprofen includes mixing coating materials with Ibuprofen to produce functionally-coated Ibuprofen. The functionally-coated Ibuprofen are then stressed mechanically and/or thermally to deform the deformable coating material, creating a continuous film surrounding the Ibuprofen. The functionally-coated Ibuprofen are then mixed with a matrix solution or suspension to form the pharmaceutical suspension. The pharmaceutical suspension comprising the functionally-coated Ibuprofen can be dosed into preformed molds, such as blister packs, and further treated to produce a dispensable pharmaceutical composition (e.g., a lyophilizate, a wafer, a tablet, etc.). In some embodiments, the dispensable pharmaceutical composition may be an orodispersible product. Ideally, a minimal amount, if any, of the Ibuprofen of the final dispensable pharmaceutical composition dissolves within the first few minutes of oral administration. This delay, or substantial reduction of Ibuprofen release, allows for the taste of the Ibuprofen to be masked when the orodispersible product is in a patient's mouth. Instead, the Ibuprofen can release once the pharmaceutical composition has passed to the gastrointestinal tract.

However, when the functionally-coated Ibuprofen are mixed into a matrix solution/suspension, the shear forces required to mix the particles into the matrix solution/suspension can erode the functional coating of the Ibuprofen. Erosion of the coating can destroy or damage the properties of the functional coating. For example, erosion of the functional coating can destroy or damage any taste-masking properties of the functional coating and allow the Ibuprofen to undergo dissolution in the oral cavity.

Accordingly, it has been discovered that hydrophobic fumed silica, as well as being used as a flow aid for the functionally-coated Ibuprofen to aid downstream processing, may also be used to provide a hydrophobic barrier layer surrounding and/or partially or fully embedded into the functionally-coated Ibuprofen. Specifically, the hydrophobic barrier layer formed by the hydrophobic fumed silica can protect one or more underlying coatings of the functionally-coated Ibuprofen during preparation of the pharmaceutical suspension and other downstream processing of the functionally-coated Ibuprofen. Thus, Ibuprofen according to some embodiments described herein may have a first, functional coating and a second, protective coating However, some pharmaceutical compositions and methods of preparing pharmaceutical compositions provided herein may include more than a first coating and a second coating. For example, some pharmaceutical compositions and methods of preparing the same may include three, four, five, six, or more coatings. Thus, the terms "first coating" and "second coating" as used herein should not be construed narrowly. As used herein, the term "first coating" refers to a functional coating of Ibuprofen, and "second coating" refers to a protective coating comprising silica. In some embodiments, functionally-coated Ibuprofen may have one or more coating layers between a "first coating" and a "second coating". In some embodiments, functionally-coated Ibuprofen may have one or more coating layers between the Ibuprofen and the "first coating". In some embodiments, a functionally-coated Ibuprofen may have one or more coating layers on top of a "second coating".

Once the functionally-coated Ibuprofen are prepared, they can be mixed into the matrix/suspension solution to form a pharmaceutical suspension for dosing. Mixing functionally-coated Ibuprofen into a matrix solution/suspension can erode the functional coating of the functionally-coated Ibuprofen. In some embodiments, to minimize this erosion, hydrophobic fumed silica can be used to form a second coating layer surrounding and/or partially embedded and/or embedded into the functionally-coated Ibuprofen.

However, coating functionally-coated Ibuprofen (i.e., Ibuprofen comprising at least a first coating, as described above) that will later be mixed into a matrix solution/suspension with hydrophobic fumed silica is not naturally intuitive. As described above, to create an orodispersible pharmaceutical composition according to embodiments described herein, the functionally-coated Ibuprofen are mixed into a matrix solution/suspension comprising a matrix former, a structure former, and a solvent (often water) to form a pharmaceutical suspension. However, a hydrophobic material is naturally resistant to mixing into a matrix solution/suspension. Accordingly, one might assume that hydrophobic fumed silica would increase the interfacial tension between the functionally-coated Ibuprofen and the matrix solution/suspension, increasing the difficulty of incorporating the functionally-coated Ibuprofen into the matrix solution/suspension and potentially causing phase separation of the pharmaceutical suspension.

Interestingly, it has been determined that hydrophobic fumed silica can be used to coat functionally-coated Ibuprofen comprising to preserve the first, functional coating without substantially interfering with the incorporation of the functionally-coated Ibuprofen into the matrix solution/suspension. As described above, a hydrophobic material in a matrix solution/suspension, such as the functionally-coated Ibuprofen covered with the hydrophobic fumed silica in the matrix solution/suspension described above, characteristically exhibits a relatively high surface tension between the hydrophobic material and the matrix solution/suspension. Accordingly, the surface tension between the hydrophobic functionally-coated Ibuprofen and the matrix solution/suspension is likely relatively high as well.

However, as discussed below, the matrix solution/suspension may comprise a matrix former such as gelatin. Some matrix formers, including gelatin, are mild surfactants, meaning that they can lower the surface tension between two materials. Accordingly, it is believed that matrix formers exhibiting surfactant-like behaviors can reduce the surface tension between the functionally-coated Ibuprofen and the matrix solution/suspension, which in turn allows for incorporation of the functionally-coated Ibuprofen into the matrix solution/suspension, while at the same time maintaining the protective properties of the hydrophobic fumed silica coating layer with respect to the first, functional coating of the functionally-coated Ibuprofen. This second coating layer comprising hydrophobic fumed silica can provide a hydrophobic barrier to the underlying first coating of the functionally-coated Ibuprofen, to protect the underlying first coating from the shear forces required to mix the functionally-coated Ibuprofen into a pharmaceutical suspension. By coating the functionally-coated Ibuprofen with a hydrophobic barrier comprising hydrophobic fumed silica, the underlying (first) coating may be protected from erosion. Further, using hydrophobic fumed silica according to described methods can prevent the matrix solution/suspension from penetrating through the coating to the Ibuprofen.

Under normal processing conditions, without a hydrophobic fumed silica coating layer, the coating of the functionally-coated Ibuprofen can erode over time under the shear forces required to mix the functionally-coated Ibuprofen into the matrix solution/suspension. However, there can be a "processing window" of two or more hours from the time the functionally-coated Ibuprofen are first mixed into the matrix solution/suspension wherein the coating can remain intact and its functionality can remain uncompromised. The exact time of this "processing window" varies and can depend upon the composition of the various components of the functionally-coated Ibuprofen, the composition of the matrix solution/suspension, the amount of material used to prepare the coating of the functionally-coated Ibuprofen, and/or the physicochemical properties of the Ibuprofen. However, with functionally-coated Ibuprofen having a second coating comprising fumed silica, this "processing window" can be extended.

In some embodiments, the pharmaceutical composition or the coated Ibuprofen can comprise from 0.5 to 35% w/w hydrophobic fumed silica. In some embodiments, the pharmaceutical composition or the coated Ibuprofen can comprise from 0.5 to 20% w/w, from 0.5 to 10% w/w, or from 0.5 to 5% w/w hydrophobic fumed silica. In some embodiments, the pharmaceutical composition or the coated Ibuprofen can comprise more than 0.5% w/w, more than 1.0% w/w, more than 1.5% w/w, more than 2.0% w/w, more than 2.5% w/w, more than 3.0% w/w, more than 4.0% w/w, more than 5.0% w/w, more than 10% w/w, more than 15% w/w, more than 20% w/w, more than 25% w/w, or more than 30% w/w hydrophobic fumed silica. In some embodiments, the pharmaceutical composition or the coated Ibuprofen can comprise less than 35% w/w, less than 25% w/w, less than 15% w/w, less than 10% w/w, less than 5.0% w/w, less than 4.0% w/w, less than 3.5% w/w, less than 3.0% w/w, less than 2.5% w/w, less than 2.0% w/w, less than 1.5% w/w, or less than 1.0% w/w hydrophobic fumed silica. The hydrophobic fumed silica may be any of Aerosil R972 silica (Degussa), CAB-O-SIL EH-5 silica (Cabot), OX-50 silica (Degussa), COSM055 (Catalyst & Chemical Ind. Co. Ltd (Japan)), TS5 silica (Cabot), and/or other suitable types of silica.

The effectiveness of the hydrophobic fumed silica-comprising protective layer can be determined by measuring the particle size of the functionally-coated Ibuprofen in the pharmaceutical suspension over time. If the hydrophobic fumed silica is effective at preserving the coating, the particle size of the functionally-coated Ibuprofen can remain constant or decrease very little over time. If ineffective, the particle size of the functionally-coated Ibuprofen can decrease more substantially over time. The particle size of the functionally-coated particles can be measured using laser diffraction, a particle analyzer such as a Malvern Mastersizer, or any other suitable means for analyzing fine particles.

The effectiveness of the hydrophobic fumed silica-comprising protective layer can also be determined by conducting dissolution testing on the functionally-coated Ibuprofen. If the hydrophobic fumed silica is effective at preserving the coating, the release amount (e.g., percent of release) of the functionally-coated Ibuprofen over time will be slower in dissolution testing. If ineffective, the release amount of the functionally-coated Ibuprofen over time will be greater. The release amount of the functionally-coated particles can be measured using dissolution testing, a spectrophotometric analyzer such as a Pion MicroDISS Profiler, or any other suitable means for conducting dissolution testing.

Minimizing the Aeration of Suspensions Comprising Ibuprofen

Embodiments provided herein may include adding a chemical compound comprising terpene and/or terpinol to the matrix solution/suspension. Specifically, embodiments of the pharmaceutical suspensions provided herein may include liquid flavors comprising terpene and/or terpinols. In some embodiments, the liquid flavor(s) may include the terpene limonene. Particular chemical compounds, and specifically the addition of liquid flavors comprising limonene, can minimize the aeration of the suspension, increase the homogeneity of the suspension, and improve the dose weight accuracy when the suspension is injected into molds. As used herein, "dose weight accuracy" and related terms refer to the ability to accurately dispense a pharmaceutical suspension into a pre-formed mold. The dose weight accuracy of the dosed pharmaceutical suspension may depend on a number of variables, including, but not limited to, homogeneity, viscosity, chemical components, dosing instrument, etc.

As described above, traditional mechanical means of anti-aeration and/or minimizing aeration have not been found to be successful due to the high viscosity of the pharmaceutical suspension. For example, applying a vacuum to the pharmaceutical suspension can cause a height of the suspension to rise because the viscous suspension "holds onto" the entrained air. Volatile formulation components may also be lost during vacuum processing. Further, traditional anti-aerating agents, such as ethanol or simethicone emulsion are similarly ineffective at anti-aerating the suspension.

Accordingly, it has been discovered that some chemical compounds, and in particular, liquid flavors comprising terpenes and/or terpinols such as limonene, can minimize the aeration of the pharmaceutical suspension when hydrophobic coated Ibuprofen are mixed in to the matrix solution/suspension. By minimizing aeration, the hydrophobic coated Ibuprofen are more efficiently and effectively dispersed throughout the pharmaceutical suspension. This increased dispersion can increase the homogeneity of the pharmaceutical suspension, the dose weight accuracy, as well as the content uniformity of the finished product.

As described above, mixing hydrophobic coated Ibuprofen into a matrix solution/suspension can generate entrained air, or air bubbles in the liquid. Because the coated Ibuprofen are hydrophobic, they have a generally low affinity for the matrix solution/suspension. Thus, instead of readily associating with and dispersing into the matrix solution/suspension, the hydrophobic coated Ibuprofen preferably associate with the entrained air. In many fluids, air bubbles typically travel to the surface of the fluid and disappear into the air above. However, because the hydrophobic coated Ibuprofen have an affinity for the entrained air, the hydrophobic coated Ibuprofen "hold onto" the air bubbles, preventing them from traveling to the surface and releasing into the air above the fluid. This causes the pharmaceutical suspension to become aerated. Aeration of the pharmaceutical suspension can cause phase separation, and thus, a non-homogeneous suspension. The phase separation can also become exaggerated upon exposure to shear forces introduced by dosing pumps. Non-homogenous pharmaceutical suspensions can cause pump seizures when passed through dosing pumps, leading to inaccurate dose weights and a lack of uniformity throughout the finished product as well as poor production efficiency through stoppages.

Additionally, pharmaceutical suspensions comprising hydrophobic coated Ibuprofen can have high viscosities due to a high loading of hydrophobic coated Ibuprofen (i.e., as much as 50 wt. % hydrophobic coated Ibuprofen). Entraining air into the pharmaceutical suspension during in-line mixing of the hydrophobic coated Ibuprofen into suspension, as described above, can increase the viscosity of the pharmaceutical suspension even further. Accordingly, not only does the phase separation and non-homogeneity of the suspension adversely impact the dose weight accuracy and uniformity of the final product, but so too does the increased viscosity.

Interestingly, it has been found that certain chemical compounds, when added to the matrix solution/suspension, can minimize the aeration of pharmaceutical suspensions comprising hydrophobic coated Ibuprofen. Particularly, chemical compounds comprising terpene and/or terpinol, according to some embodiments provided herein, may minimize the amount of the entrained air in pharmaceutical suspensions caused by in-line mixing of hydrophobic coated Ibuprofen into matrix solutions/suspensions. For example, suspensions comprising liquid flavors comprising terpenes and/or terpinols, even in relatively low concentrations, can minimize aeration of pharmaceutical suspensions. Specifically, it has been discovered that matrix solutions/suspensions comprising one or more liquid flavor comprising limonene can minimize aeration in pharmaceutical suspensions during in-line mixing of hydrophobic coated Ibuprofen. Other chemical compounds including terpenes and terpinols have been shown to be successful at minimizing aeration of pharmaceutical suspensions as well. For example, chemical compounds including terpenes such as limonene, carvone, humulene, taxadiene, and squalene may be suitable for minimizing the aeration of the pharmaceutical suspension. Terpinol may also be a suitable anti-aerating agent. In some embodiments, pure terpenes and/or pure terpinols may be used as an anti-aerating agent. In some embodiments, a liquid flavor comprising terpene and/or terpinol may be used as an anti-aerating agent. In some embodiments, other suitable chemical compounds comprising terpene and/or terpinol may be used as an anti-aerating agent.

One challenge posed with some chemical compounds comprising terpene and/or terpinol, such as some liquid flavors, is that they tend to be relatively oily. As with conventional oil and water, these oily chemical compounds may not readily disperse into a matrix solution/suspension. However, as discussed below, matrix solutions/suspensions according to embodiments here may include gelatin as a matrix former. Gelatin is inherently a mild surfactant. Surfactants can lower the surface tension between two materials. Accordingly, in some embodiments, the gelatin of the matrix solution/suspension can reduce the surface tension between the oily chemical compounds and the matrix solution/suspension. This can allow adequate incorporation of the oily chemical compounds, such as liquid flavors, into the matrix solution/suspension.

Under normal processing conditions, without use of chemical compounds comprising terpene and/or terpinol, the coating of the hydrophobic coated Ibuprofen erodes with time due to shear forces required to mix the hydrophobic coated Ibuprofen into the matrix solution/suspension to form the pharmaceutical suspension. However, there is a “processing window” of two or more hours wherein the coating retains significant functionality. The exact time of this “processing window” varies for each product, and can depend upon the composition of the components of the hydrophobic coated Ibuprofen, the composition of the matrix solution/suspension, the amount of material used to prepare the hydrophobic coated Ibuprofen, the physicochemical properties of Ibuprofen, and/or the conditions of mixing. Unfortunately, in the presence of chemical compounds comprising terpenes and/or terpinols this “processing window” can be significantly reduced due to interactions between these chemical compounds and the coating of the hydrophobic coated Ibuprofen. These interactions may damage the functional properties of the coating. For example, interactions between liquid flavors and the coating of the hydrophobic coated Ibuprofen may damage any taste-masking functionality of the coating. That said, it has been discovered that there is a threshold chemical compounds (i.e., liquid flavor) concentration below which the chemical compound does not significantly compromise the coating, yet the “processing window” is not reduced so much that the coating of the hydrophobic coated Ibuprofen significantly erodes. Accordingly, this optimal amount of chemical compound comprising terpene and/or terpinol adequately minimizes the aeration of the pharmaceutical suspension, resulting in a homogenous pharmaceutical suspension that can be accurately dosed into molds to yield a uniform final product.

Additionally, chemical compounds comprising terpene and/or terpinol, and specifically liquid flavors comprising limonene, have the potential to lower the freezing point of the pharmaceutical suspension, which could lead to melting defects for products further processed by freeze-drying. In particular, limonene has a freezing point of −74° C. However, no melting defects have been observed during the preparation of the disclosed product, and thus at least some chemical compounds comprising terpene and/or terpinol do not impact the pharmaceutical suspension such that the freezing and freeze-drying process steps downstream are adversely affected. The absence of melting defects under the present circumstances is believed to be due to the high solids content of the suspension, which helps to maintain the structure of the product, even in the presence of a freezing point depressing agent (i.e., limonene).

Matrix solution/suspension compositions according to embodiments described herein may include a matrix former, a structure former, an anti-aerating agent, a viscosity modifier, and/or a solvent.

In some embodiments, an amount of a chemical compounds comprising terpene and/or terpinol (i.e., an anti-aerating agent) in the matrix solution/suspension, the pharmaceutical suspension, or the pharmaceutical composition may be from 0.001 to 5.0% w/w. In some embodiments, an amount of chemical compounds comprising terpene and/or terpinol (i.e., an anti-aerating agent) in the matrix solution/suspension, the pharmaceutical suspension, or the pharmaceutical composition can be 1-5% w/w, 1-4% w/w, 1-3% w/w, 1-2% w/w, 0.05 to 3.0% w/w, 0.1 to 2.0% w/w, or 0.5 to 1.0% w/w. In some embodiments, more than 0.001% w/w, more than 0.01% w/w, more than 0.05% w/w, more than 0.1% w/w, more than 0.3% w/w, more than 0.5% w/w, more than 0.8% w/w, more than 1.0% w/w, more than 1.5% w/w, more than 2.0% w/w, more than 2.5% w/w, more than 3.0% w/w, more than 3.5% w/w, more than 4.0% w/w, or more than 4.5% w/w of chemical compounds comprising terpene and/or terpinol (i.e., an anti-aerating agent) are in the matrix solution/suspension, the pharmaceutical suspension, or the pharmaceutical composition. In some embodiments, less than 5.0% w/w, less than 4.5% w/w, less than 4.0% w/w, less than 3.5% w/w, less than 3.0% w/w, less than 2.5% w/w, less than 2.0% w/w, less than 1.5% w/w, less than 1.0% w/w, less than 0.8% w/w, less than 0.6% w/w, less than 0.3% w/w, or less than 0.1% w/w of chemical compounds comprising terpene and/or terpinol (i.e., an anti-aerating agent) are in the matrix solution/suspension, the pharmaceutical suspension, or the pharmaceutical composition. In some embodiments, a suitable anti-aerating agent may include orange flavor, strawberry flavor, mint flavor, raspberry flavor, licorice flavor, orange flavor, lemon flavor, lime flavor, grapefruit flavor, caramel flavor, vanilla flavor, cherry flavor, grape flavor, mixed fruit flavor, tutti-frutti flavor or any combination thereof.

Minimizing Agglomeration Examples

Several trials were performed to evaluate the effectiveness of removing excess coating material from coated Ibuprofen by sieving and to optimize the coating ratios and dosing ratios. Disintegration times of pharmaceutical compositions containing various coated Ibuprofen were measured under various conditions to study the effect of sieving excess coating material. It may be reasonably assumed that removing excess coating material can minimize agglomeration of the coating material. Optimizing the coating and dosing ratios can also aid in minimizing coating material agglomeration. In turn, minimizing the amount of agglomeration can help maintain desired disintegration times and/or dissolution rates of the pharmaceutical composition and coated Ibuprofen. Accordingly, disintegration time is used as a metric to evaluate the amount of agglomeration in the following Examples. In some embodiments, the 50° C. accelerated disintegration data can be indicative of the presence of unsieved, excess coating material.

Additionally, coating ratio and dosing ratio information is provided for the Examples below. Coating ratio refers to the amount of coating materials to the amount of uncoated Ibuprofen. Dosing ratio refers to the amount of coated Ibuprofen to the matrix solution/suspension comprising of all the inactive ingredients.

Example 1: Ibuprofen was coated with carnauba wax with a coating ratio of 26:74. A dosing ratio of 40:60 was used to produce freeze dried tablets. Four separate batches of tablets were tested—Batch 1-3 over a period of 2 months, and Batch 4 over a period of 6 months. These batches of tablets were each tested at ICH (International Council for Harmonisation of Technical Requirements for Pharmaceuticals for Human Use) stability conditions of 25° C./60% RH, 30° C./65% RH, and 40° C./75% RH and sampled at one month and two months for Batches 1, 2, and 3. Additionally, each batch was exposed to a 50° C. stress condition to provide accelerated data at both two weeks and at four weeks for each study. Table 1 below provides the disintegration time data for Batches 1-3 of the two-month study of coated ibuprofen.

TABLE 1

| | | | | | | | | | | |
|---|---|---|---|---|---|---|---|---|---|---|
| | | | | | Carnauba Wax (Dosing Ratio 40:60) (2-Month Study) | | | | | |
| Batch Nos | Batch | Strength | Initial DT | 2 Week 50° C. | 4 Week 50° C. | 1 Month 25° C./ 60% RH | 1 Month 30° C./ 65% RH | 1 Month 40° C./ 75% RH | 2 Month 25° C./ 60% RH | 2 Month 30° C./ 65% RH | 2 Month 40° C./ 75% RH |
| 1 | Z3876/128 | 400 MG | <2 s | <4 s | <10 s | <4 s | <4 s | <4 s | <3 s | <4 s | <7 s |
| 2 | Z4630/97 | 50 MG | <2 s | <4 s | <7 s | <2 s | <2 s | <2 s | <2 s | <2 s | <15 s |
| 3 | Z4630/101 | 50 MG | <3 s | <3 s | <4 s | <1 s | <2 s | <3 s | <2 s | <2 s | <2 s |

Figure 4A:
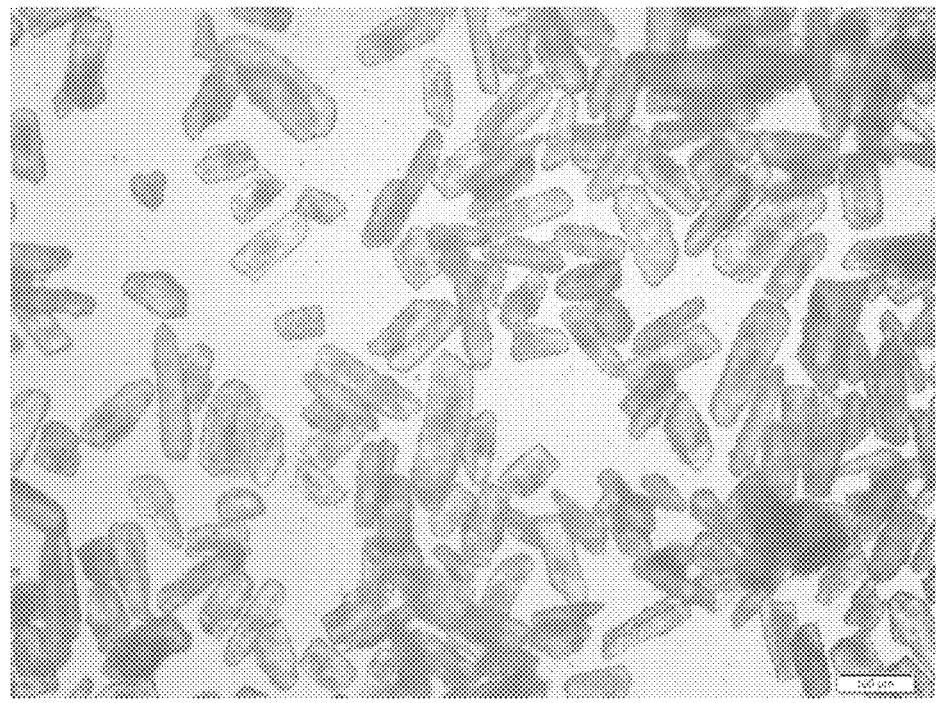
FIGS. 4A-4J are a series of photomicrographs taken of sieved coated Ibuprofen for Examples 1-4.
Figure 4B:
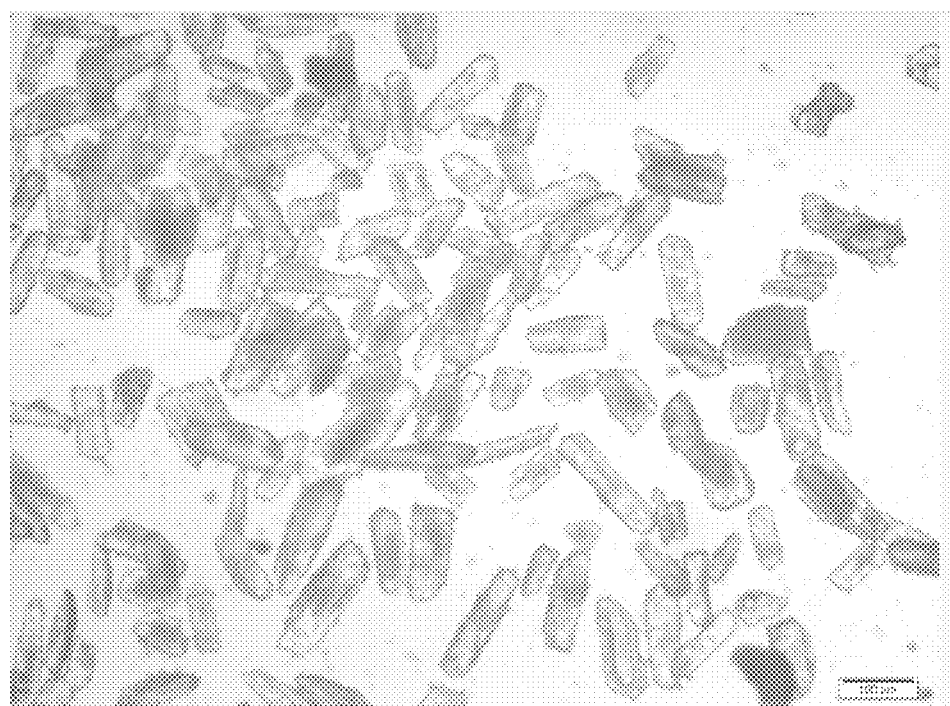

Coated Ibuprofen for Batch 2 was poorly sieved post Ibuprofen coating. Microscopic examination (FIG. 4B) of the sieved coated Ibuprofen showed the presence of an excess amount of unbound coating material. Microscopic examination of the sieved coated Ibuprofen also showed that the Ibuprofen was poorly coated. As shown in the last column of Table 1, this batch exhibited a significantly longer disintegration time at the 40° C./75% RH stability testing conditions after two-months. (The initial disintegration time was less than two seconds, and the disintegration time at two months was almost 15 seconds). Accordingly, this result supports the hypothesis that presence of an excess amount of unbound coating material in the pharmaceutical product is responsible for extended disintegration time over time (as the pharmaceutical product ages) because of the agglomeration of the unbound coating material during storage.

Figure 4C:

Conversely, coated Ibuprofen for Batch 3 was sieved well post Ibuprofen coating. Microscopic examination (FIG. 4C) of the sieved coated Ibuprofen showed that the Ibuprofen was well coated since there is an absence of unbound coating material. The disintegration time for the samples of this batch changed very little over the two-month period for any of the ICH stability conditions. (The disintegration time throughout the two-month study fluctuated between approximately one second and approximately three seconds). This supports the hypothesis that minimizing the presence of excess unbound coating material by sieving, for example, will help to prevent the agglomeration of coating material in pharmaceutical product when place on storage, particularly at higher temperatures over time.

The coated Ibuprofen for Batch 1 was sieved post Ibuprofen coating. Batch 1 exhibited similar disintegration time of less than 2 seconds compared to Batch 2 and 3 for the initial time data points. However, at the 40C/75% RH stability testing conditions after two-months, the disintegration time increased to approximately 7 seconds or less. When stored for 4 weeks at 50° C., the disintegration time increased to approximately 10 seconds or less. This suggests that the sieving process for this batch did not sufficiently remove the excess coating material, hence the presence of residual unbound coating material. Batch 2 experienced even more unbound coating material and agglomeration on storage to a greater extent than that of Batch 1. Microscopic examination (FIG. 4A) of the sieved coated Ibuprofen showed that the Ibuprofen particles were moderately well coated with residue amount of unbound coating material present.

Table 2 below shows the disintegration time data for the six-month study of coated Ibuprofen (i.e., Batch 4).

TABLE 2

Carnauba Wax (Dosing Ratio 40:60) (6-Month Study)

| Batch Nos | Batch | Strength | Initial | 2 Week 50° C. | 4 Week 50° C. | 1 Month 25° C./ 60% RH | 1 Month 30° C./ 65% RH | 1 Month 40° C./ 75% RH |
|---|---|---|---|---|---|---|---|---|
| 4 | Z3876/131 | 200 MG | <5 s | <20 s | <13 s | <5 s | <4 s | <5 s |

| Batch | 3 Month 25° C./ 60% RH | 3 Month 30° C./ 65% RH | 3 Month 40° C./ 75% RH | 6 Month 25° C./ 60% RH | 6 Month 30° C./ 65% RH | 6 Month 40° C./ 75% RH |
|---|---|---|---|---|---|---|
| 4 | <4 s | <3 s | <4 s | <2 s | <2 s | <2 s |

Figure 4D:
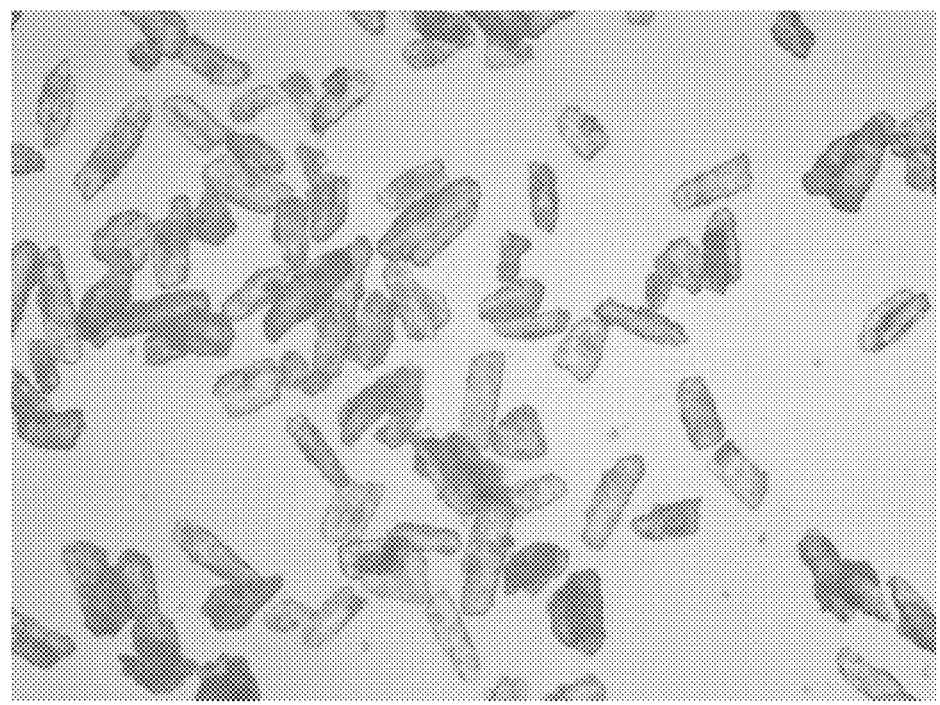

The coated Ibuprofen for Batch 4 was sieved post Ibuprofen coating. Batch 4 of Table 2 did not show much change in disintegration time throughout the duration of the six-month study. The initial disintegration time of Batch 4 was approximately five seconds, and the final disintegration time of the 25° C./60% RH samples was approximately two seconds; the 30° C./65% RH samples approximately two seconds, and the 40° C./75% RH samples approximately two seconds. However, an increase was seen when stored at 50° C. Since no increase was seen in the tablets stored at temperatures of 40° C. and below, this suggests that sieving has removed most of the unbound excess coating material but with sufficient residue amount that agglomerate when the tablets were placed at 50° C. Microscopic examination (FIG. 4D) showed that the sieved coated Ibuprofen showed that the Ibuprofen were moderately well coated with residue amount of unbound coating material present.

Figure 4E:
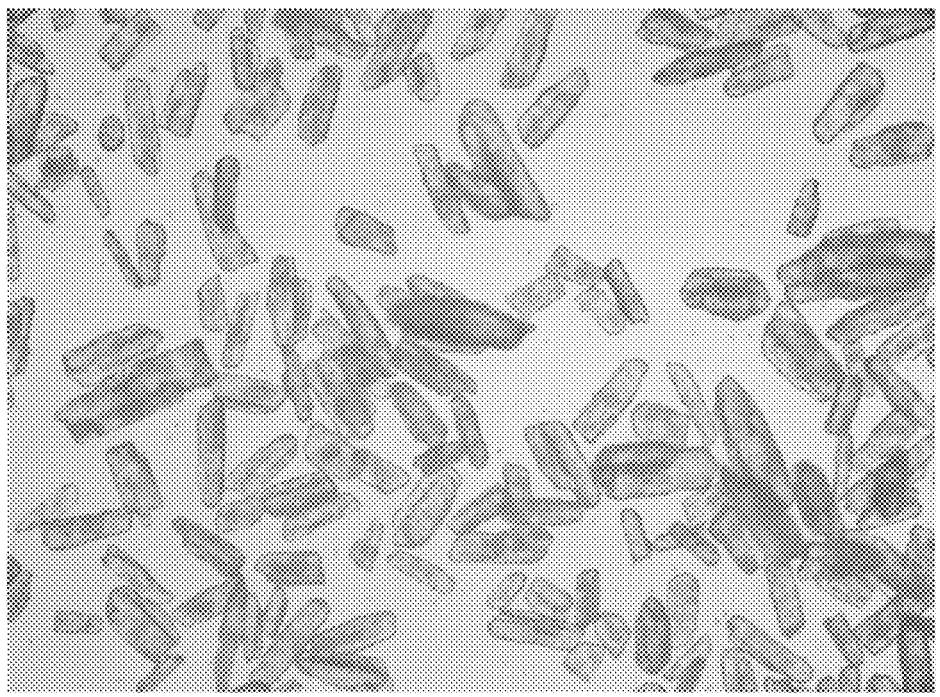

Example 2: Ibuprofen was coated with Sasol (synthetic) wax with a theoretical coating ratio of 26:74. The coated Ibuprofen was sieved after coating. A dosing ratio of 40:60 was used to produce freeze dried tablets and tested over two months. The Ibuprofen strength was 200 mg. Each batch was tested at ICH stability conditions of 25° C./60% RH, 30° C./65% RH, and 40° C./75% RH. Additionally, the samples were exposed to a 50° C. stress condition to provide accelerated data at two weeks and at four weeks during the study. Table 3 below provides the disintegration time data for the 40:60 dosing ratio two month study of coated Ibuprofen. Microscopic examination (FIG. 4E) of the sieved coated Ibuprofen showed that the Ibuprofen were moderately well coated with a small amount of unbound coating material.

TABLE 3

Sasol Wax (Dosing Ratio 40:60) Ibuprofen Strength: 200 mg

| Batch Nps | Batch | Initial DT | 2 Week 50° C. | 4 Week 50° C. | 1 Month 25° C./ 60% RH | 1 Month 30° C./ 65% RH | 1 Month 40° C./ 75% RH | 2 Month 25° C./ 60% RH | 2 Month 30° C./ 65% RH | 2 Month 40° C./ 75% RH |
|---|---|---|---|---|---|---|---|---|---|---|
| 5 | Z3876/138 | <3 s | <3 s | <4 s | <2 s | <2 s | <5 s | <4 s | <4 s | <4 s |

Batch 5 of Table 3 shows no substantial change in the disintegration time during the two months of the study, nor at the 50° C. accelerated conditions. Specifically, the initial disintegration time of Batch 5 was approximately three seconds, and the disintegration time at two months for all three ICH stability conditions (25° C./60% RH, 30° C./65% RH, and 40° C./75% RH) was approximately four seconds. The disintegration time for the 50° C. accelerated condition at two weeks was approximately three seconds and at 4 weeks was approximately four seconds. Based on the 50° C. data, a small residue amount of unbound excess coating material may be present. If so, this small amount of unbound excess coating material does not cause a significant amount of agglomeration on storage, since the disintegration time does not increase much, if at all. This compares well with Batch 3 in Example 1 where a different wax was used. These 2 examples demonstrate that if the unbound excess coating material is efficiency removed by sieving, agglomeration of the coating material in the pharmaceutical product on storage can be minimized or prevented, in particular at higher temperatures and upon prolonged storage period.

Figure 4F:
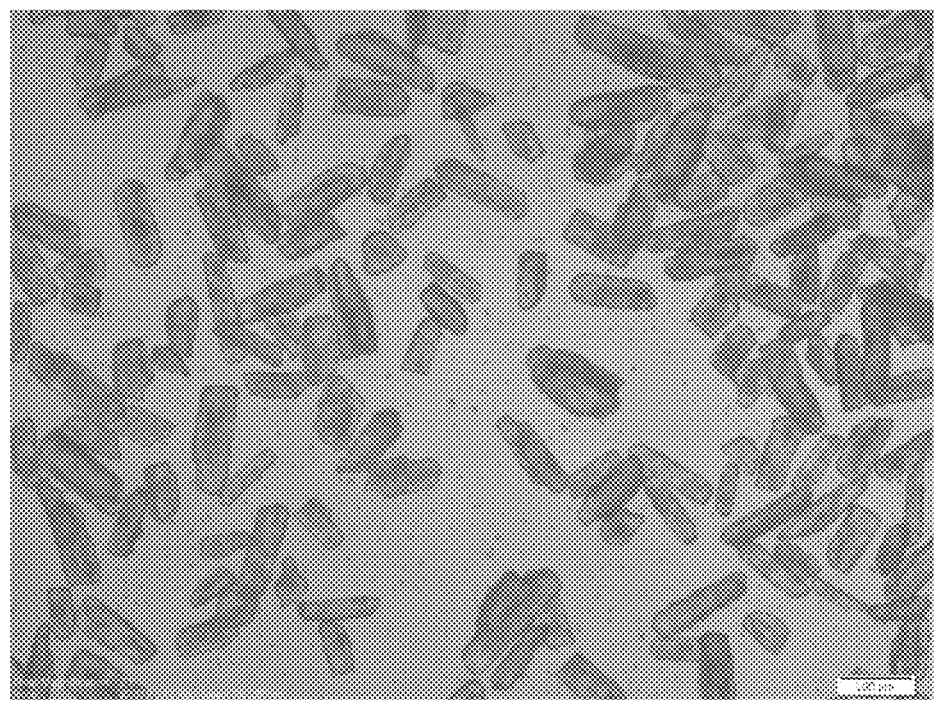

Example 3: Ibuprofen was coated with Sasol (synthetic) wax with a theoretical coating ratio of 26:74. The coated ibuprofen was then sieved after coating. A dosing ratio of 50:50 was used to produce freeze dried tablets and tested over three months. The Ibuprofen strength was 200 mg. As above in Examples 1 and 2, each batch was tested at ICH stability conditions of 25° C./60% RH, 30° C./65% RH, and 40° C./75% RH. The samples were also exposed to a 50° C. stress condition to provide accelerated data at two weeks and at four weeks during each study. Table 4, below, provides data for the three-month study of 50:50 Sasol wax-coated Ibuprofen. Microscopic examination (FIG. 4F) of the sieved coated API for Batch 6 showed the Ibuprofen were coated well and with some unbound coating material.

Neither Batch 6 nor Batch 7 showed significant change in disintegration time over the course of the three month study. Specifically, the initial disintegration time of the samples of Batch 6 was approximately one second, and the final three-month disintegration time for each of the three ICH stability conditions (25° C./60% RH, 30° C./65% RH, and 40° C./75% RH) was approximately two seconds. The disintegration time for both the two-week and the four-week accelerated 50° C. condition for Batch 6 was approximately two seconds.

The initial disintegration time for the samples of Batch 7 was approximately two seconds, and the final three-month disintegration time for the 25° C./60% RH and 30° C./65% RH ICH stability conditions was approximately two seconds. The final three-month disintegration time for the 40° C./75% RH ICH stability condition was approximately three seconds. The disintegration time for both the two-week and the four-week accelerated 50° C. condition was approximately five seconds. A high coating ratio of 50:50 can increase the amount of excess unbound coating material when left unsieved. Although both batches used a higher dosing ratio of 50:50, which means a high loading of the coated Ibuprofen and any unbound excess coating material, these data inferred that the sieving process of the coated Ibuprofen has been effective in removing the unbound excess coating materials to minimize agglomeration.

Figure 4G:
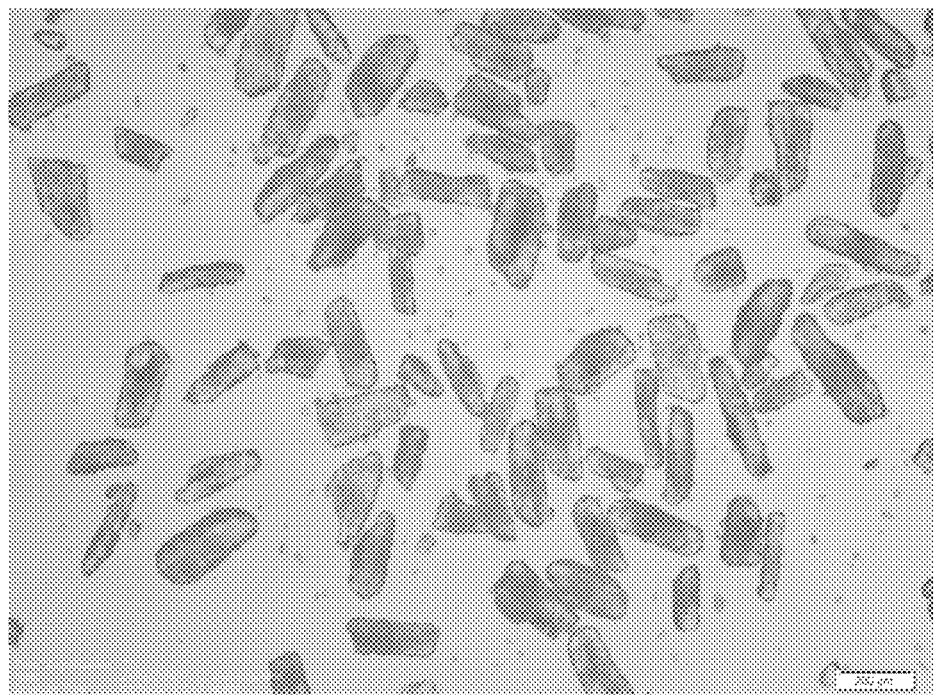
Figure 4H:
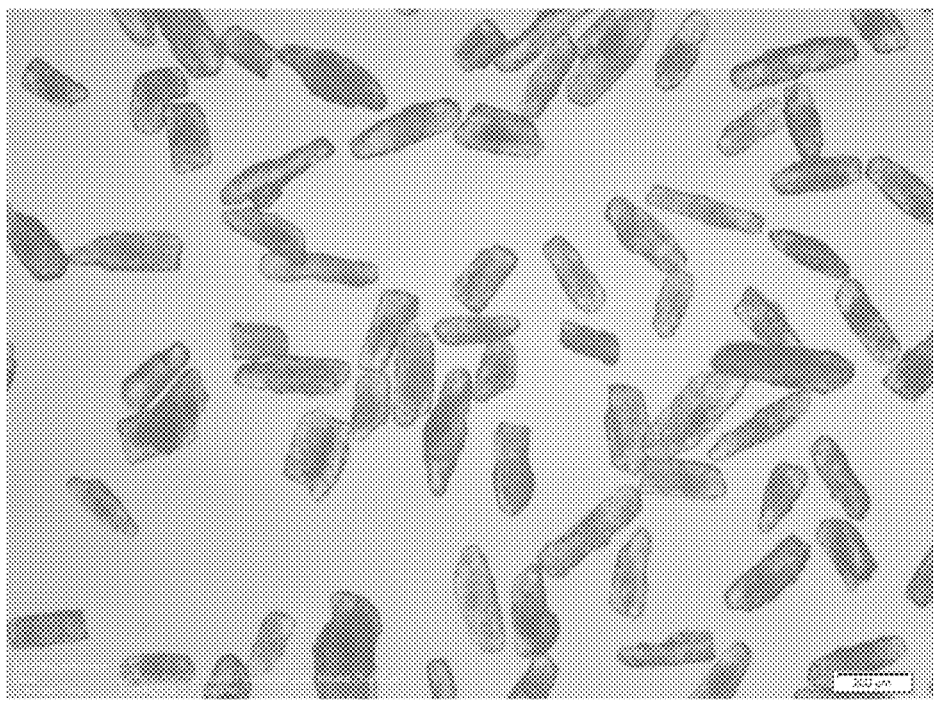
Figure 4I:
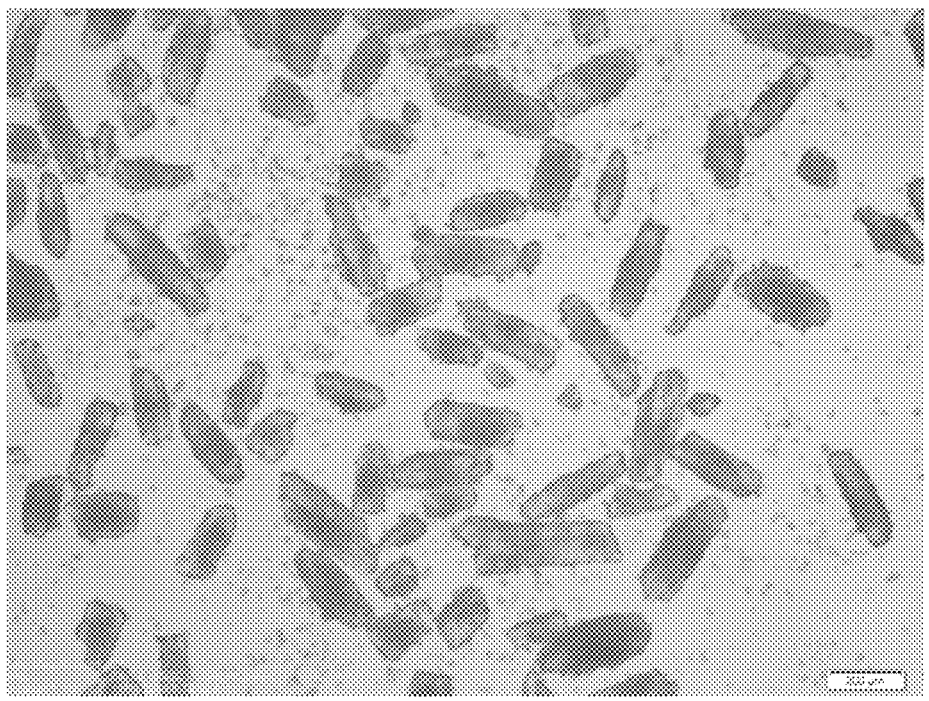
Figure 4J:
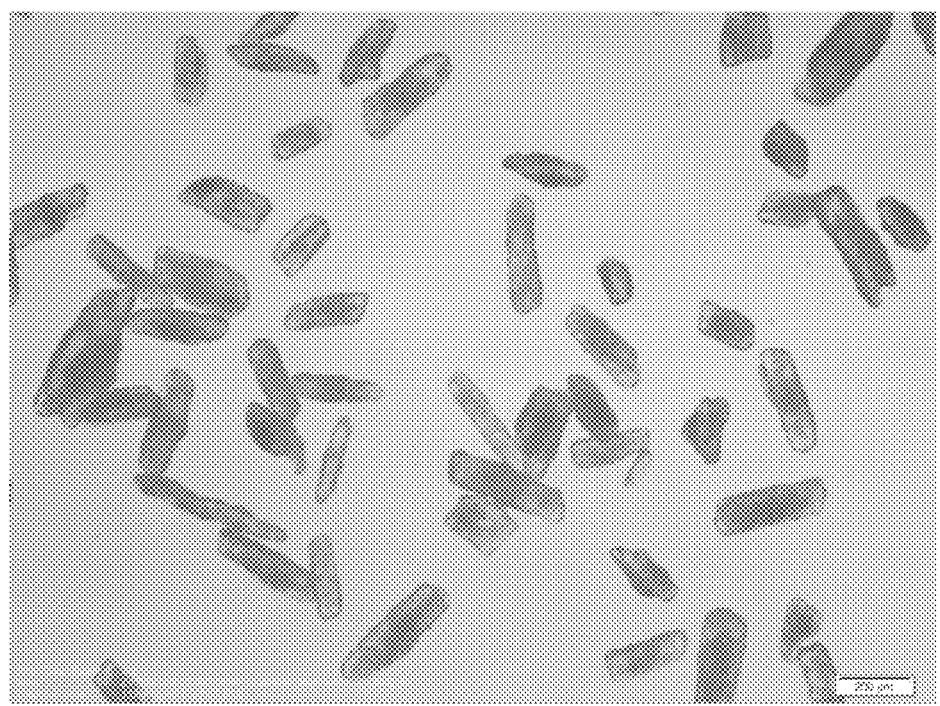

Example 4: Ibuprofen was coated with Carnuba Wax at a theoretical coating ratio of 22.5:77.5 and 30:70. A dosing ratio of 30:70 was used to produce freeze dried tablets and study over a period of 2 months. The Ibuprofen strength was 200 mg. The batches were stored in an oven at 40° C. Tablets were tested for disintegration time at the initial, Day 25, and 2 month time points. Table 5 below provides the disintegration times for the study. Microscopic examination of the unsieved coated Ibuprofen (FIGS. 4G and 4H) and sieved coated Ibuprofen (FIGS. 4I and 4J). The Ibuprofen were well coated. Sieved samples have no unbound coating material present.

TABLE 4

Sasol Wax (Dosing Ratio 50:50) Ibuprofen Strength: 200 mg

| Batch | Batch Nos | Initial DT | 2 Week 50° C. | 4 Week 50° C. | 1 Month 25° C./60% | 1 Month 30° C./ 65% RH | 1 Month 40° C./ 75% RH |
|---|---|---|---|---|---|---|---|
| 6 | Z3876/142 | <1 s | <2 s | <2 s | <2 s | <2 s | <2 s |
| 7 | Z3876/141/1 | <2 s | <5 s | <5 s | <2 s | <3 s | <3 s |

| Batch | 2 Month 25° C./ 60% RH | 2 Month 30° C./ 65% RH | 2 Month 40° C./ 75% RH | 3 Month 25° C./ 60% RH | 3 Month 30° C./ 65% RH | 3 Month 40° C./ 75% RH |
|---|---|---|---|---|---|---|
| 6 | <2 s | <1 s | <2 s | <2 s | <2 s | <2 s |
| 7 | <2 s | <2 s | <3 s | <2 s | <2 s | <3 s |

TABLE 5

Carnuba Wax (Dosing Ratio 30:70) Ibuprofen Strength: 200 mg

| Batch | Bach Nps | Coated API | Coating Ratio | Initial | Day 24 At 40° C. | 2 Month At 40° C. |
|---|---|---|---|---|---|---|
| 8 | Z4750/186/2a | Unsieved | 22.5:77.5 | 5 s | 2 s | 2 s |
| 9 | Z4750/186/4a | Sieved | 22.5:77.5 | 4 s | 3 s | 3 s |
| 10 | Z4750/186/6a | Unsieved | 30:70 | 1 s | 2 s | 2 s |
| 11 | Z4750/186/8a | Sieved | 30:70 | 2 s | 3 s | 3 s |

Batch 8-11 show that using a dosing ratio of 30:70 for coated Ibuprofen, either unsieved (Batches 8 and 10) or sieved (Batches 9 and 11), the disintegration times of the tablets stored at 40° C. has not increased over time. This supports the hypothesis that by reducing the dosing ratio; such as to 30:70, the amount of excess unbound wax is sufficiently reduced to a level that can minimize agglomeration of the excess unbound material when stored at higher temperatures over time.

The overall summary of results from the above examples are tabulated the Table 6.

TABLE 6

Overall Summary of Results for Batches 1-11.

| Batch Nos | Batch | Drug | Strength (mg) | Coating Ratio | Dosing Ratio | Sieving of Coated API | Coating Assessment (Microscopy) | Unbounded Excess Wax (Microscopy) | Disintegration Time at 40° C./75% RH at 1/2/3/6 mths | Disintegration time at 50° C. at 2/4 wk |
|---|---|---|---|---|---|---|---|---|---|---|
| 1 | Z3876/128 | Ibuprofen | 400 | 26:74 | 40:60 | Sieved | Moderate | Present | <4-7 s | <4-10 s |
| 2 | Z4630/97 | Ibuprofen | 50 | 26:74 | 40:60 | Sieved (poor) | Poor | Present | <2-15 s | <4-7 s |
| 3 | Z4630/101 | Ibuprofen | 50 | 26:74 | 40:60 | Sieved (well) | Good | Absent | <2-3 s | <3-4 s |
| 4 | Z3876/131 | Ibuprofen | 200 | 26:74 | 40:60 | Sieved | Moderate | Present | <2-5 s | <13-20 s |
| 5 | Z3876/138 | Ibuprofen | 200 | 26:74 | 40:60 | Sieved | Good | Present | <4-5 s | <3-4 s |
| 6 | Z3876/142 | Ibuprofen | 200 | 26:74 | 50:50 | Sieved | Good | Present | <2 s | <2 s |
| 7 | Z3876/141/1 | Ibuprofen | 200 | 25:75 | 50:50 | Sieved | No Photo | No Photo | <3 s | <5 s |
| 8 | Z4750/186/2a | Ibuprofen | 200 | 22.5:77.5 | 30:70 | Unsieved | Good | Present | <2 s | No data |
| 9 | Z4750/186/4a | Ibuprofen | 200 | 22.5:77.5 | 30:70 | Sieved (well) | Good | Absent | <3 s | No data |
| 10 | Z4750/186/6a | Ibuprofen | 200 | 30:70 | 30:70 | Unsieved | Good | Present | <2 s | No data |
| 11 | Z4750/186/8a | Ibuprofen | 200 | 30:70 | 30:70 | Sieved | Good | Absent | <3 s | No data |

Preserving Functionally-Coated Ibuprofen Examples

Example 5: Hydrophobic fumed silica was used to coat functionally-coated Ibuprofen according to embodiments described herein. Specifically, the hydrophobic fumed silica that was used was Aerosil R972 ("Aerosil"). Two different concentrations of Aerosil R972 were tested-1.5% w/w and 1.0% % w/w. The size of the functionally-coated Ibuprofen were evaluated over a 6-hour holding period, during which they were subjected to low shear mixing.

Figure 5:
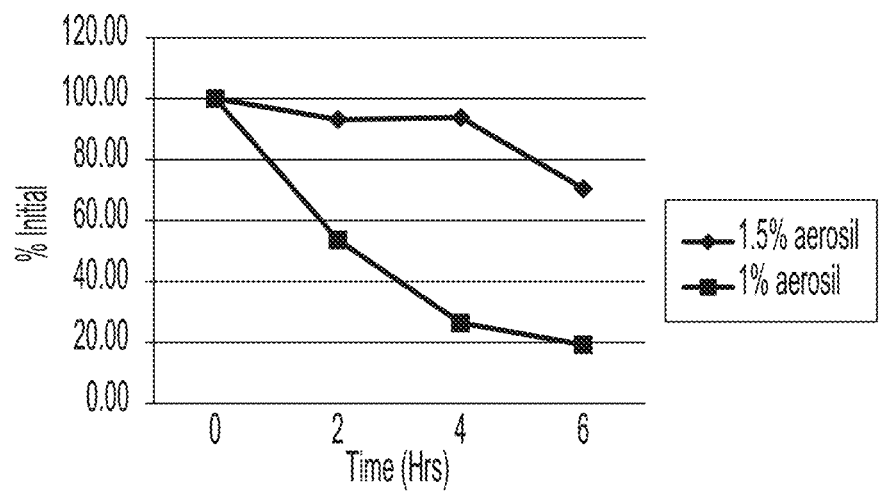
FIG. 5 is a graph providing an evaluation of d10 particle size of functionally-coated Ibuprofen comprising a second protective coating of different concentrations of silica, according to some embodiments.
Figure 6:
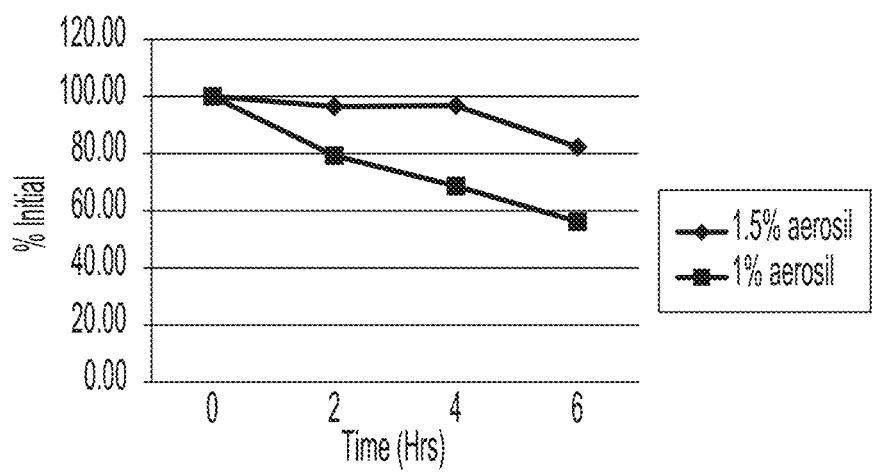
FIG. 6 shows a graph providing an evaluation of d50 particle size of functionally-coated Ibuprofen comprising a second protective coating of different concentrations of silica, according to some embodiments.
Figure 7:
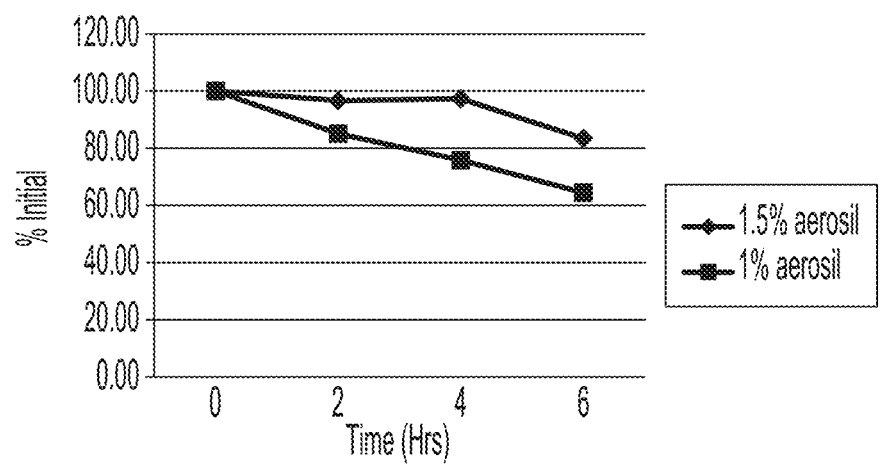
FIG. 7 shows a graph providing an evaluation of d90 particle size of functionally-coated Ibuprofen comprising a second protective coating of different concentrations of silica, according to some embodiments.

FIGS. 5, 6, and 7 provide evaluations of d10 particle size, d50 particle size, and d90 particle size, respectively, over a period of 6 hours. Generally speaking, a particle size expressed in terms of its d10 means that 10 percent of the particles in a given amount of sample lie below a given particle size. Accordingly, a particle size expressed in terms of its d50 means that 50 percent of the particles in a given amount of sample lie below a given particle size, and a particle size expressed in terms of its d90 means that 90 percent of the particles in a given amount of sample lie below a given particle size.

As shown in FIG. 5, the greater concentration of silica (1.5% w/w) was more effective at maintaining the original particle size, and thus maintaining the coating, than the lesser concentration of silica (1.0% w/w). Specifically, during the 6-hour period, the functionally-coated Ibuprofen comprising 1.5% w/w Aerosil lost approximately 30% of their original size, whereas the functionally-coated Ibuprofen comprising 1.0% w/w Aerosil lost approximately 80% of their original particle size.

FIG. 6 demonstrates that again the greater concentration of silica (1.5% w/w Aerosil) was more effective at maintaining the original functionally-coated Ibuprofen particle size, and thus preserving the functional coating, than the lesser concentration of silica (1.0% w/w Aerosil). Specifically, during a period of 6 hours, the functionally-coated Ibuprofen comprising 1.5% w/w Aerosil lost almost 20% of their original size, whereas the functionally-coated Ibuprofen comprising 1.0% w/w Aerosil lost approximately 45% of their original functionally-coated API particle size.

FIG. 7 also shows that the greater concentration of silica (1.5% w/w Aerosil) was more effective at maintaining the original functionally-coated Ibuprofen particle size, and thus preserving the functional coating of the functionally-coated Ibuprofen, than the lesser concentration of silica (1.0% w/w Aerosil). Specifically, during the 6-hour period, the functionally-coated Ibuprofen comprising 1.5% w/w Aerosil lost almost 15% of their original size, whereas the functionally-coated Ibuprofen comprising 1.0% w/w Aerosil lost approximately 35% of their original particle size.

Additionally, as the particle size of the functionally-coated Ibuprofen decreased, a separate population of particles comprising a particle size of 5 μm to 20 μm appeared and increased with time. These particles are believed to be non-deformable coating material particles embedded within the deformed, continuous coating material prior to erosion of the coating due to shear forces. Accordingly, as the coating erodes, and the particle size of the functionally-coated Ibuprofen decreases, the population size of these smaller particles increases as the deformed coating material surrounding them erodes, causing these non-deformable particles to release from the functionally-coated Ibuprofen.

Overall, these trials suggest that 1.5% w/w Aerosil coating the functionally-coated Ibuprofen may increase the "processing window" to approximately 4 hours, instead of the 2 hour "processing window" that exists without the silica. Within the first four hours of processing in suspension and comprising a second, outer coating comprising 1.5% w/w Aerosil, the functionally-coated Ibuprofen exhibit little, if any, erosion of the coating.

Example 6: Hydrophobic fumed silica was used to coat functionally-coated Ibuprofen according to embodiments described herein. Specifically, the hydrophobic fumed silica that was used was Aerosil R972 ("Aerosil"). Five different concentrations of Aerosil R972 were tested-0.0% w/w, 1.5% w/w, 2.5% w/w, 5.0% w/w and 10.0% w/w. The release amount of the functionally coated Ibuprofen was evaluated using dissolution testing (i.e., dissolution media of 0.01% SDS in pH 7.2 phosphate buffer, media temperature of 37° C., and media volume of 10 ml (Ibuprofen)).

Figure 8:
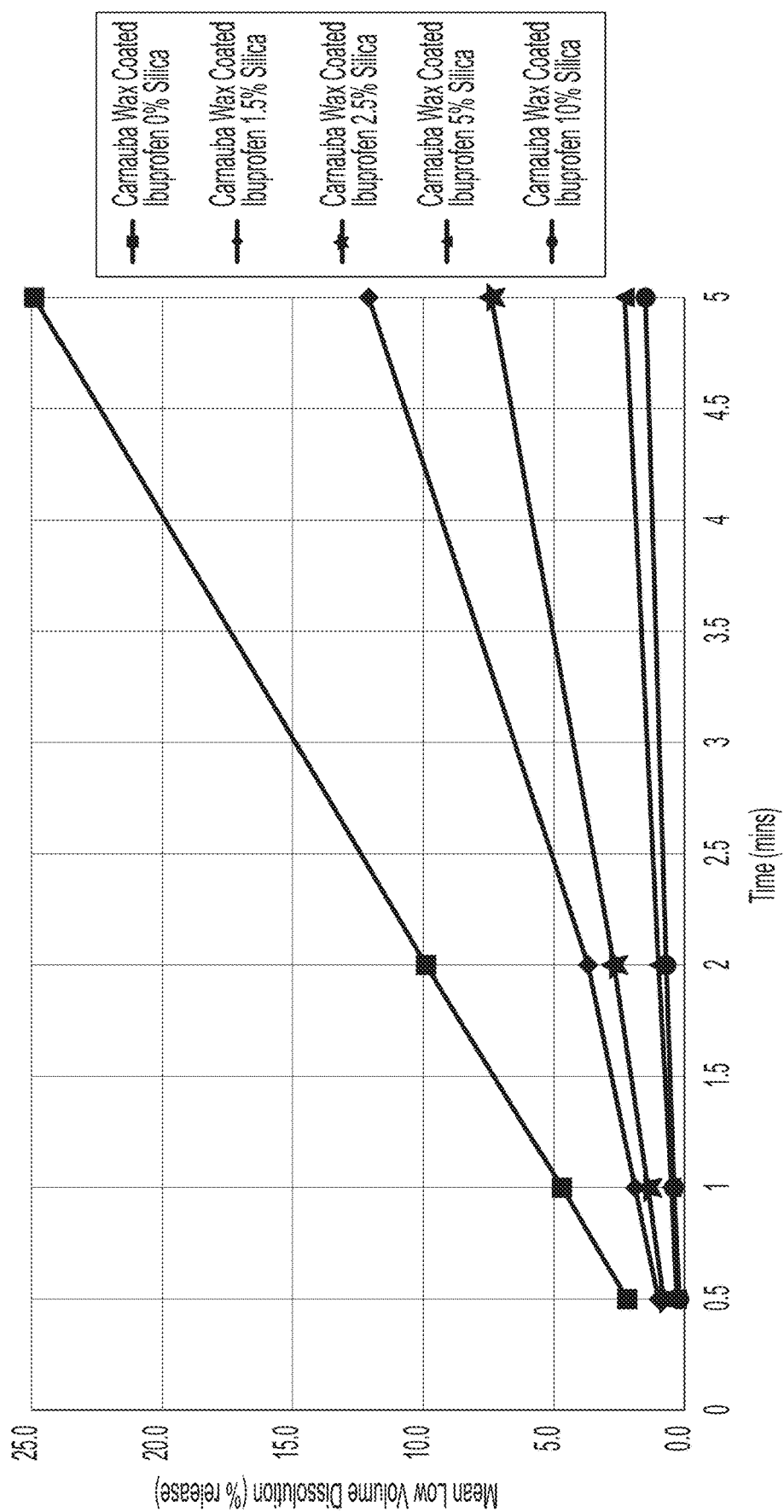
FIG. 8 shows a graph of low volume dissolution of Ibuprofen coated with carnauba wax with varying levels of hydrophobic fumed silica, according to some embodiments.
Figure 9:
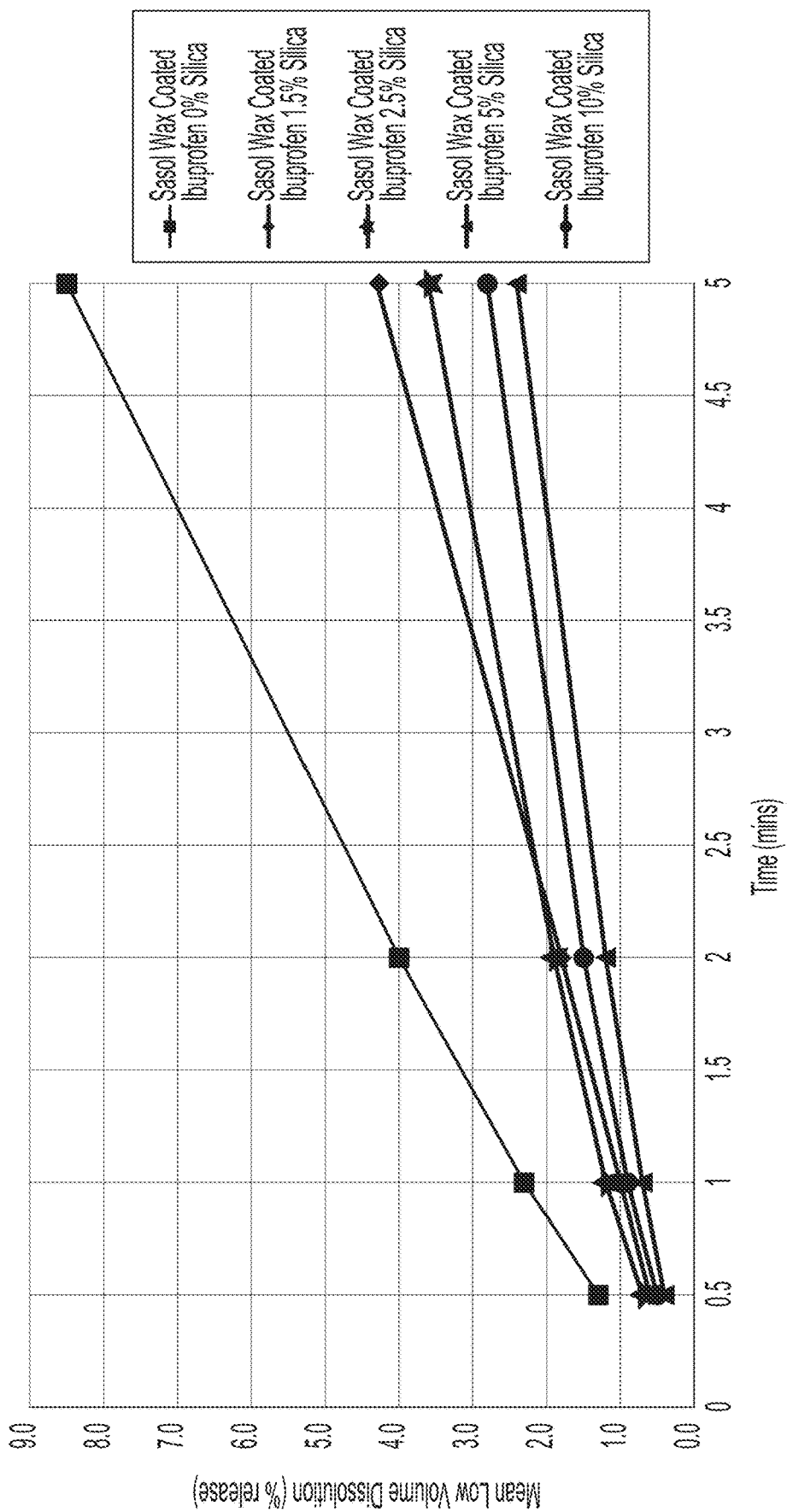
FIG. 9 shows a graph of low volume dissolution of Ibuprofen coated with Sasol (synthetic) wax comprising varying levels of hydrophobic fumed silica, according to some embodiments.

FIGS. 8 and 9 provide evaluations of release amount conducted on the functionally coated Ibuprofen, over a period of either 5 or 30 minutes. Generally speaking, a low volume dissolution result expressed in terms of its % release means that 'x' percent of the weight of material added has dissolved into solution.

FIG. 8 shows release data for Ibuprofen coated with carnauba wax and various amounts of hydrophobic silica. As shown in the Figure, greater concentrations of silica (up to 10.0% w/w) were more effective at providing a slower release rate in dissolution testing, and thus maintaining the coating, than the lesser concentrations of silica. Specifically, during the 5 minute testing period, the functionally-coated Ibuprofen (i.e., Ibuprofen coated with carnauba wax) comprising 10.0% w/w Aerosil exhibited a 1.5% release after 5 minutes, whereas the functionally-coated Ibuprofen comprising 0.0% w/w Aerosil exhibited a 24.9% release. Functionally-coated Ibuprofen comprising intermediate levels of Aerosil (i.e., 1.5% w/w, 2.5% w/w and 5.0% w/w) showed dissolution results after 5 minutes of 12.1% release, 7.4% release and 2.3% release, respectively.

Figure 10:
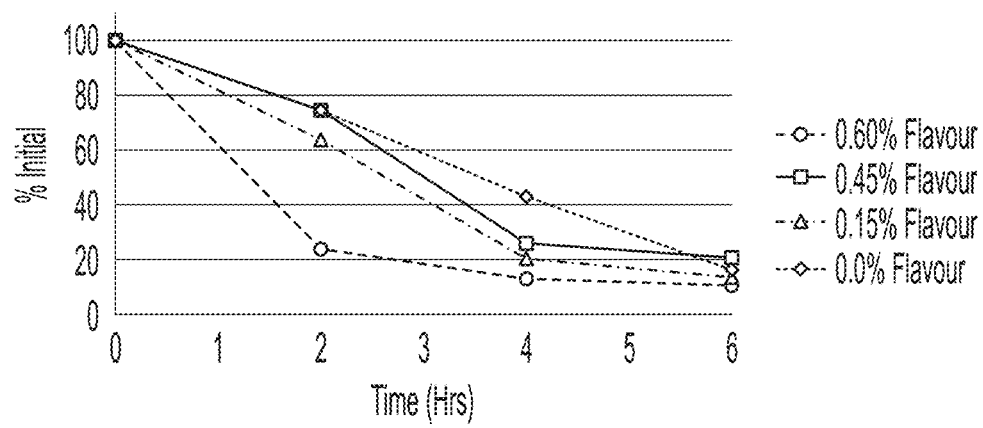
FIG. 10 shows a graph providing an evaluation of d10 particle size of hydrophobic coated Ibuprofen with various concentrations of liquid flavor.

FIG. 9 provides release data for Ibuprofen coated with Sasol (synthetic) wax and various levels of hydrophobic silica. FIG. 10 also shows that greater concentrations of silica (up to 10.0% w/w) were more effective at providing a slower release rate in dissolution testing, and thus maintaining the coating, than the lesser concentrations of silica. Specifically, during the 5 minute testing period, the functionally-coated Ibuprofen (i.e., Ibuprofen coated with synthetic wax) comprising 10.0% w/w Aerosil exhibited a 2.8% release after 5 minutes, whereas the functionally-coated Ibuprofen comprising 0.0% w/w Aerosil shows an 8.5% release. Functionally-coated Ibuprofen comprising intermediate levels of Aerosil (i.e., 1.5% w/w, 2.5% w/w and 5.0% w/w) gave dissolution results after 5 minutes of 4.3% release, 3.6% release and 2.4% release, respectively.

Minimizing Aeration Examples

The effectiveness of chemical compounds comprising terpene and/or terpinol at minimizing aeration can be determined in part by measuring the particle size of the hydrophobic coated Ibuprofen in pharmaceutical suspension over time. If the chemical compound is effective, the aeration of the suspension will be adequately low and the particle size of the hydrophobic coated Ibuprofen will remain constant or decrease very little over time. If ineffective, the aeration of the suspension will be higher than desired and the particle size of the hydrophobic coated Ibuprofen can decrease more substantially over time. The extent of aeration of the suspension is assessed by measurement of height of the foam in the mixing vessel. The particle size of the functionally-coated particles can be measured using laser diffraction, a particle analyzer such as a Malvern Mastersizer, or any other suitable means for analyzing fine particles.

Example 7: A series of suspension mixes were manufactured by mixing the coated Ibuprofen in the matrix solution/suspension containing various levels of limonene, orange flavor, and strawberry flavor. The height of the foam from these suspension is summarized in Table 7, 8, and 9 respectively.

TABLE 7

Height of foam from mixes containing various levels of limonene.

| Concentration of limonene (% w/w) | Foam Height (mm) |
|---|---|
| 0 | 5 |
| 0.15 | 2 |
| 0.30 | 1 |
| 0.6 | 1 |

TABLE 8

Height of foam from mixes containing various levels of orange flavor.

| Concentration of orange flavor (% w/w) | Foam Height (mm) |
|---|---|
| 0 | 5 |
| 0.15 | 1 |
| 0.30 | 0 |
| 0.6 | 0 |

TABLE 9

Height of foam from mixes containing various levels of strawberry flavor.

| Concentration of strawberry flavor (% w/w) | Foam Height (mm) |
|---|---|
| 0 | 5 |
| 0.15 | 3 |
| 0.30 | 3 |
| 0.6 | 3 |

The results in Tables 7 and 8 show that the addition of limonene and orange flavor at level 0.15% w/w and above minimize the aeration. For strawberry (Table 9), it also reduced aeration but not to the same extent.

Figure 11:
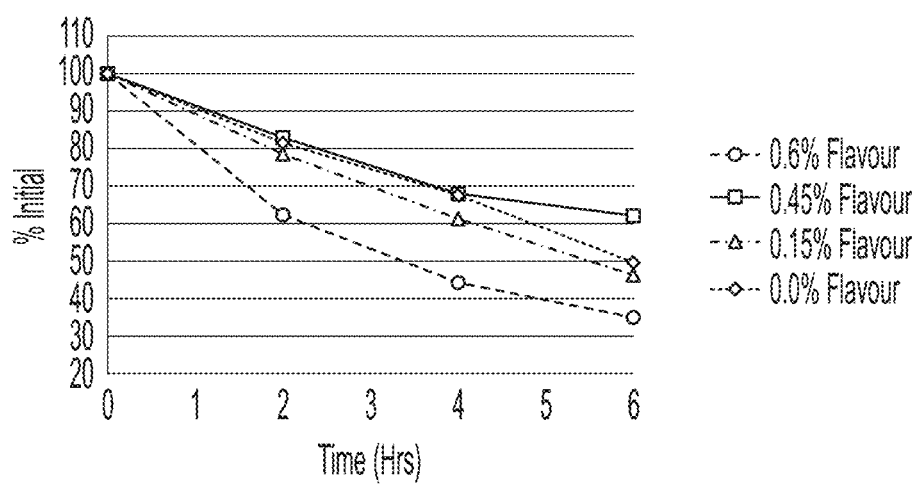
FIG. 11 shows a graph providing an evaluation of d50 particle size of hydrophobic coated Ibuprofen with various concentrations of liquid flavor.
Figure 12:
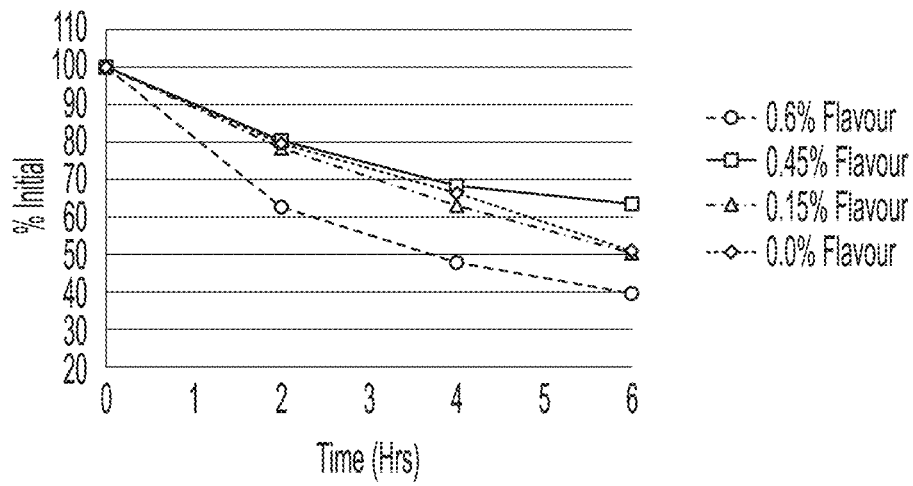
FIG. 12 shows a graph providing an evaluation of d90 particle size of hydrophobic coated Ibuprofen with various concentrations of liquid flavor.

Example 8: FIGS. 10, 11, and 12 show the decrease in particle size (d10, d50, and d90, respectively) of hydrophobic coated Ibuprofen in a pharmaceutical suspension comprising various concentrations of liquid orange flavor. A particle size expressed in terms of its d10 means that 10 percent of the particles in a given volume of sample lie below a given particle size. Accordingly, a d50 particle size represents 50 percent of the particles in a given volume of sample lie below a given particle size, and a d90 particle size represents 90 percent of the particles in a given volume of sample lie below a given particle size. Specifically, FIGS. 3-5 show test results for suspension formulations containing hydrophobic coated Ibuprofen and liquid orange flavor at concentrations including 0.0%, 0.15%, 0.45%, and 0.60% w/w, held over a period of up to 6 hours with low shear mixing.

At concentrations of up to 0.45% w/w of orange flavor (including 0.15% w/w), the decrease in d10, d50, and d90 particle size within the first 2 hour "processing window" is largely similar to that of a pharmaceutical suspension comprising hydrophobic coated Ibuprofen without any liquid flavor (0% liquid flavor). However, at a concentration of 0.6% w/w liquid orange flavor, the coating of the hydrophobic coated Ibuprofen is readily removed and a rapid decrease in particle size is observed. Further, at a liquid orange flavor concentration of 0.3% w/w, the aeration of the suspension was sufficiently low with only little, if any damage to the coating of the coated ibuprofen, and only minimal decrease in particle size of the hydrophobic coated Ibuprofen.

Figure 13:
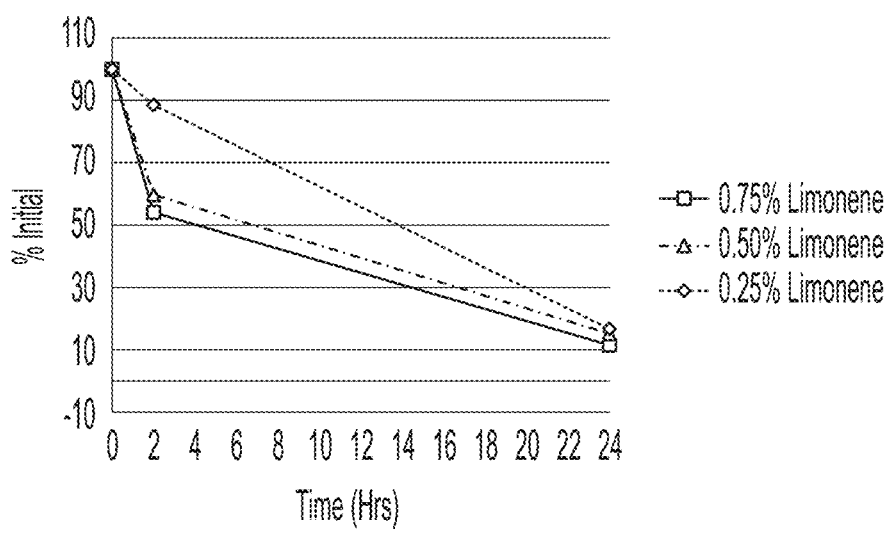
FIG. 13 shows a graph providing an evaluation of d10 particle size of hydrophobic coated Ibuprofen with various concentrations of pure limonene.
Figure 14:
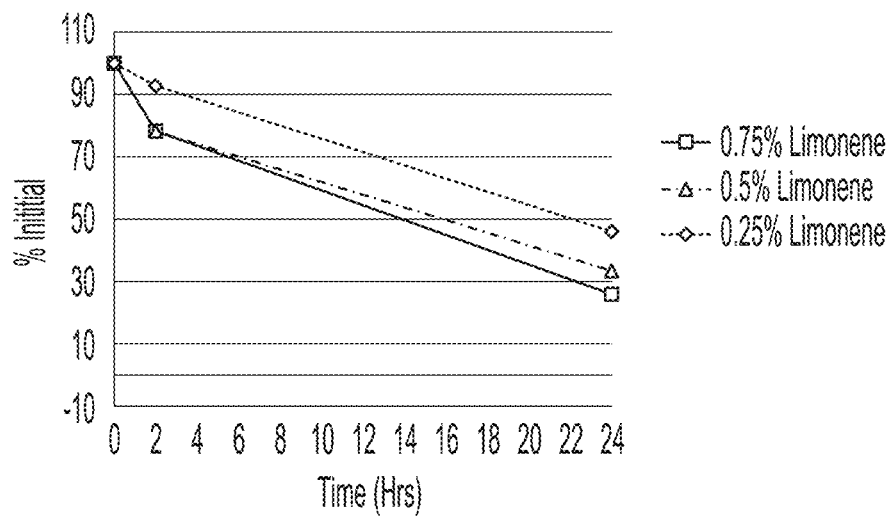
FIG. 14 shows a graph providing an evaluation of d50 particle size of hydrophobic coated Ibuprofen with various concentrations of pure limonene.
Figure 15:
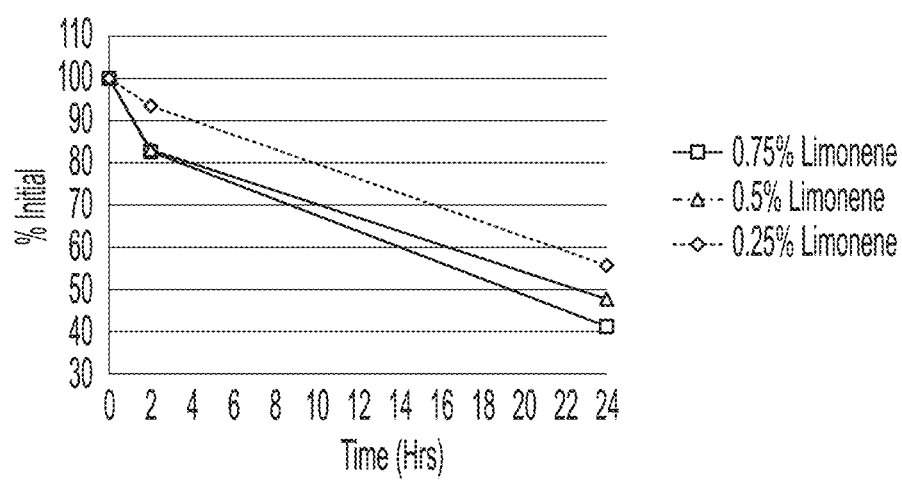
FIG. 15 shows a graph providing an evaluation of d90 particle size of hydrophobic coated Ibuprofen with various concentrations of pure limonene.

Example 9: FIGS. 13, 14, and 15 provide data on the decrease in d10, d50, and d90 particle size, respectively, of the hydrophobic coated Ibuprofen for the specific component limonene, which is found in some liquid flavors. These tests were conducted to explore the behaviors of the specific component of the liquid flavor, limonene, on hydrophobic coated Ibuprofen in suspension. Note that the concentrations of limonene shown in the Figures are significantly greater than the concentration of limonene that would be present if a liquid flavor was used. In FIGS. 13-15, pure limonene was used in concentrations of 0.25% w/w, 0.45% w/w, and 0.75% w/w and tested over a period of 24 hours. As shown across all three Figures, a limonene concentration of 0.25% w/w had a much less deleterious effect on the coating of the hydrophobic coated Ibuprofen particle size than limonene concentration of 0.45% w/w and 0.75% w/w. Further, the pharmaceutical suspensions tested with 0.25% w/w limonene comprised a sufficiently low amount of aeration. Accordingly, these tests confirm that limonene of the liquid orange flavor tested in FIGS. 3-5 are at least partially responsible for minimizing the aeration of the pharmaceutical suspension and subsequently eroding the coating of the hydrophobic coated Ibuprofen in relatively high quantities and/or at relatively high exposure times.

Figure 16:
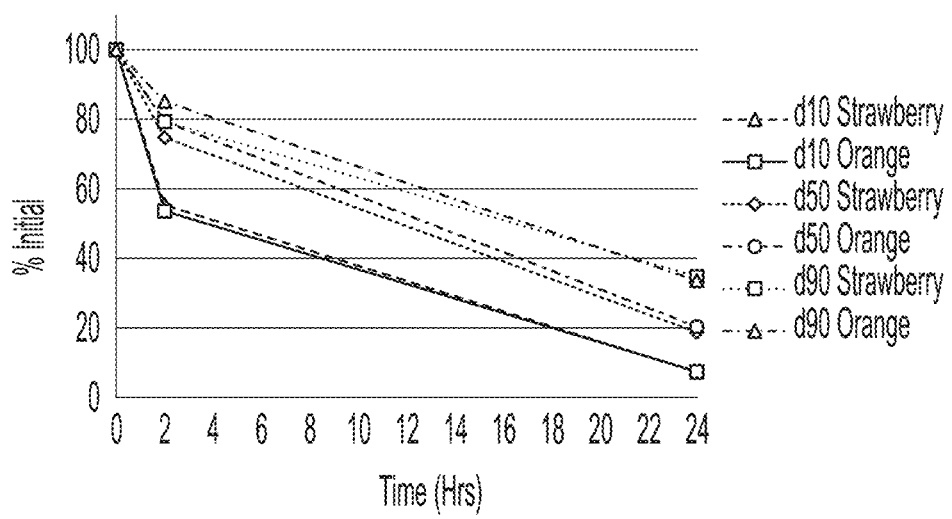
FIG. 16 shows a graph comparing the various particle size analyses of hydrophobic coated Ibuprofen with strawberry and orange liquid flavors.

Example 10: FIG. 16 shows testing data of two different liquid flavors—strawberry and orange. D10, d50, and d90 particle sizes of the hydrophobic coated Ibuprofen were tested for both strawberry liquid flavor and orange liquid flavor. Both strawberry and orange liquid flavors comprise limonene. As shown in the Figure, both flavors behave similarly with regards to hydrophobic coated Ibuprofen particle size. The d10 particle samples showed a greater amount of particle size decrease within the first two hours of the trial than the d50 and d90 particle size samples. The d50 and d90 particle size samples exhibited less of a particle size decrease within the same two-hour period. However, this observation is consistent with the data of d10, d50, and d90 particle sizes of the previously-discussed examples.

Additionally, it was observed in all trials that as the particle size of the hydrophobic coated API (Ibuprofen) particles decreased, a separate population of particles comprising a particle size of 5 µm to 20 µm appeared and increased with time. These particles are believed to be non-deformable coating material particles embedded within the deformed, continuous coating material prior to erosion of the coating due to shear forces. Accordingly, as the coating erodes, and the particle size of the hydrophobic coated Ibuprofen decreases, the population size of these smaller particles increases as the deformed coating material surrounding them erodes, causing these non-deformable particles to release from the hydrophobic coated Ibuprofen.

Overall, these trials show that by optimizing the amount of the terpene limonene to add to the pharmaceutical suspension comprising hydrophobic coated Ibuprofen, the amount of aeration in the suspension can be minimized to permit downstream processing while at the same time not having an adverse effect on the coating of the hydrophobic coated Ibuprofen (as determined by the particle size of the hydrophobic coated Ibuprofen.)

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The invention claimed is:

1. A coated active pharmaceutical ingredient ("API") consisting of:
    a wax surrounding an API; and
    a silica partially embedded in and/or embedded in the wax, wherein the silica produces a slower dissolution profile for the API as compared to API without silica.

2. The coated API of claim 1, wherein the coated API consists of 0.5-10% w/w silica.

3. The coated API of claim 1, wherein the coated API consists of 10-30% w/w wax.

4. The coated API of claim 1, wherein the wax consists of one or more of carnauba wax, synthetic wax, or candelilla wax.

5. The coated API of claim 1, wherein the API consists of Ibuprofen.

* * * * *